(12) United States Patent
Bowman et al.

(10) Patent No.: US 8,846,777 B2
(45) Date of Patent: Sep. 30, 2014

(54) THIOL-VINYL AND THIOL-YNE SYSTEMS FOR SHAPE MEMORY POLYMERS

(75) Inventors: Christopher Bowman, Boulder, CO (US); Neil Cramer, Boulder, CO (US); Robin Shandas, Boulder, CO (US); Devatha P. Nair, Lakewood, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 104 days.

(21) Appl. No.: 12/988,983

(22) PCT Filed: Apr. 22, 2009

(86) PCT No.: PCT/US2009/041359
§ 371 (c)(1),
(2), (4) Date: Jan. 5, 2011

(87) PCT Pub. No.: WO2009/132070
PCT Pub. Date: Oct. 29, 2009

(65) Prior Publication Data
US 2011/0144227 A1    Jun. 16, 2011

Related U.S. Application Data

(60) Provisional application No. 61/047,026, filed on Apr. 22, 2008.

(51) Int. Cl.
| | | |
|---|---|---|
| *C03C 25/10* | (2006.01) | |
| *C08G 18/67* | (2006.01) | |
| *C08J 3/28* | (2006.01) | |
| *C08F 2/46* | (2006.01) | |
| *C08G 61/04* | (2006.01) | |
| *C09D 175/16* | (2006.01) | |
| *C08F 290/06* | (2006.01) | |
| *C08G 18/10* | (2006.01) | |
| *B29C 59/16* | (2006.01) | |
| *C08F 2/50* | (2006.01) | |
| *C08F 2/48* | (2006.01) | |
| *A61L 27/50* | (2006.01) | |

(52) U.S. Cl.
CPC ............ *C08G 18/672* (2013.01); *C09D 175/16* (2013.01); *C08F 290/067* (2013.01); *C08G 18/10* (2013.01); *B29C 59/16* (2013.01); *C08F 2/50* (2013.01); *C08F 2/48* (2013.01); *C08F 2/46* (2013.01); *A61L 27/50* (2013.01)
USPC .................. 522/96; 522/90; 522/113; 522/1; 520/1

(58) Field of Classification Search
CPC .... C08G 18/672; C08G 18/10; C09D 175/16; C08F 290/067; C08F 2/50; C08F 2/46; C08F 2/48; B01F 2215/0049; B29G 59/16; A61L 27/50
USPC ............... 522/96, 90, 113, 1; 520/1
See application file for complete search history.

(56) References Cited

U.S. PATENT DOCUMENTS

| | | | |
|---|---|---|---|
| 3,966,794 | A | 6/1976 | Larsen |
| 4,883,699 | A | 11/1989 | Aniuk et al. |
| 5,126,425 | A | 6/1992 | Sasagawa et al. |
| 5,234,456 | A | 8/1993 | Silvestrini |
| 5,304,606 | A | 4/1994 | Yamamoto |
| 5,506,300 | A | 4/1996 | Ward et al. |
| 5,591,199 | A | 1/1997 | Porter et al. |
| 5,599,291 | A | 2/1997 | Balbierz et al. |
| 5,674,242 | A | 10/1997 | Phan et al. |
| 5,895,718 | A | 4/1999 | Ishimura et al. |
| 5,964,744 | A | 10/1999 | Balbierz et al. |
| 6,022,550 | A | 2/2000 | Watanabe |
| 6,156,842 | A | 12/2000 | Hoenig et al. |
| 6,160,084 | A | 12/2000 | Langer et al. |
| 6,388,043 | B1 | 5/2002 | Langer et al. |
| 6,426,134 | B1 | 7/2002 | Lavin et al. |
| 6,530,951 | B1 | 3/2003 | Bates et al. |
| 6,550,480 | B2 | 4/2003 | Feldman et al. |
| 6,720,402 | B2 | 4/2004 | Langer et al. |
| 6,887,266 | B2 | 5/2005 | Williams et al. |
| 6,986,855 | B1 | 1/2006 | Hood et al. |
| 7,208,550 | B2 | 4/2007 | Mather et al. |
| 7,217,744 | B2 | 5/2007 | Lendelein et al. |
| 7,377,939 | B2 * | 5/2008 | Williams et al. ............. 623/1.46 |
| 7,427,410 | B2 | 9/2008 | Hubbell et al. |

(Continued)

FOREIGN PATENT DOCUMENTS

| | | |
|---|---|---|
| EP | 0242874 | 10/1987 |
| EP | 0802237 | 10/1997 |
| EP | 1801140 | 6/2007 |
| JP | 09-302040 | * 11/1997 |
| WO | WO 00/64956 | 2/2000 |
| WO | WO 00/64964 | 11/2000 |
| WO | WO 2004/073690 | 9/2004 |
| WO | WO 2006/071520 | 7/2006 |
| WO | WO 2006/086646 | 8/2006 |
| WO | WO 2006/098757 | 9/2006 |

(Continued)

OTHER PUBLICATIONS

Baer et al. (Dec. 2006) "Shape-memory behavior of thermally stimulated polyurethane for medical applications," J Appl Polym Sci 103:3882-3892.

(Continued)

*Primary Examiner* — Ling Choi
*Assistant Examiner* — Jessica E Whiteley
(74) *Attorney, Agent, or Firm* — Lathrop & Gage LLP

(57) ABSTRACT

A variety of biomedical devices are provided which include thiol-ene or thiol-yne shape memory polymers. The biomedical devices of the invention are capable of exhibiting shape memory behavior at physiological temperatures and may be used in surgical procedures. Methods of making the devices of the invention are also provided.

16 Claims, 5 Drawing Sheets

(56) References Cited

U.S. PATENT DOCUMENTS

| | | | |
|---|---|---|---|
| 7,575,740 | B2 | 8/2009 | Molenberg et al. |
| 2004/0030062 | A1 | 2/2004 | Mather et al. |
| 2005/0119733 | A1* | 6/2005 | Wiliams et al. ............ 623/1.49 |
| 2006/0036045 | A1 | 2/2006 | Wilson et al. |
| 2006/0052547 | A1 | 3/2006 | Jethmalani et al. |
| 2006/0064170 | A1 | 3/2006 | Smith et al. |
| 2006/0095134 | A1 | 5/2006 | Trieu et al. |
| 2006/0154195 | A1 | 7/2006 | Mather et al. |
| 2006/0188546 | A1 | 8/2006 | Giroux |
| 2007/0142605 | A1 | 6/2007 | Bojkova et al. |
| 2008/0081763 | A1 | 4/2008 | Swetlin et al. |
| 2008/0085946 | A1* | 4/2008 | Mather et al. ..................... 522/4 |
| 2008/0214774 | A1 | 9/2008 | Brown et al. |
| 2008/0319132 | A1 | 12/2008 | Lendlein et al. |
| 2009/0248141 | A1 | 10/2009 | Shandas |
| 2010/0192959 | A1 | 8/2010 | Shandas |

FOREIGN PATENT DOCUMENTS

| | | | |
|---|---|---|---|
| WO | WO 2007/015815 | | 2/2007 |
| WO | WO 2007/115208 | | 10/2007 |
| WO | WO 2008/042157 | | 4/2008 |
| WO | WO 2008/051254 | | 5/2008 |
| WO | WO 2008/077123 | | 6/2008 |
| WO | WO 2009/010423 | * | 1/2009 |
| WO | WO 2009/020797 | | 2/2009 |

OTHER PUBLICATIONS

Bowman et al. (2006) "Hybrid Methacrylate/Thiol-ene System for Novel Dental Resins," The IADR General Session & Exhibition (Jun. 28-Jul. 1, 2006) Program [online][retrieved on Apr. 1, 2009] Retrieved from the internet: <URL:http://iadr.confex.com/iadr/2006Brisb/techprogram/abstract_80567.htm>.

Buckley et al. (Jan. 2007) "Novel triol-crosslinked polyurethanes and their thermorheological characterization as shape-memory materials," Polymer 48(5):1388-1396.

Carioscia et al. (Oct. 2007) "Thiol-Norbornene Materials: Approaches to Develop High Tg Thiol-Ene Polymers," Journal of Polymer Science Part-A Polymer Chemistry 45:5686-5696.

Cramer et al. (2001), "Kinetics of Thiol-Ene and Thiol-Acrylate Photopolymerizations with Real-Time Fourier Transform Infrared," J. Polymer Science, Part A: Polymer Chemistry 39:3311-3319.

Cramer et al. (2003), "Thiol-ene Photopolymerization Mechanism and Rate Limiting Step Changes for Various Vinyl Functional Group Chemistries," Macromolecules 36(21)7964-7969.

Duerig et al. (1999) "An overview of nitinol medical applications," Mater Sci Eng, A273-275, p. 149.

Fairbanks et al. (online Dec. 2008), "Thiol-Yne Photopolymerizations: Novel Mechanism, Kinetics, and Step-Growth Formation of Highly Cross-Linked Networks," Macromolecules 42(1):211-217.

Fu et al. (Jan. 2007) "The designable elastic modulus of 3-D fabric reinforced biocomposites," Materials Letters 61(2)330-333, ISSN 0167-577X, DOI: 10.1016/j.matlet.2006.04.057.

Gall et al. (2005) "Thermomechanics of the shape memory effect in polymers for biomedical applications," J. Biomed. Mater. Res.—Part A 73:339.

Ghosh, Samaresh (Apr. 2004) "Recent research and development in synthetic polymer based drug delivery systems," Journal of Chemical Research 241-246(6).

Hernandez (2002) [retrieved May 3, 2013] "The Stability and Relative Reactivity of Urethane/Epoxy Acrylate-based Systems Containing a Thiol-functional Monomer," UHD Proceedings [online]' Retrieved from: http://www.uhd.edu/academic/colleges/sciences/scholars/files/proceedings2002.pdf.

Hoyle et al. (2004), "Thiol-Enes: Chemistry of the Past with Promise for the Future," J. Polymer Science: Part A: Polymer Chemistry 43:5501-5338.

Jing Cui, Karl Kratz and Andreas Lendlein (2009) "Shape-Memory Properties of Radiopaque Micro-Composites from Amorphous Polyether Urethanes Designed for Medical Application," MRS Proceedings 1190, 1190-NN03-22 doi:10.1557/PROC-1190-NN03-22.

International Search Report and Written Opinion for PCT/US09/41359, mailed Aug. 13, 2009.

Jeon et al. (2000) "Shape memory and nanostructure in poly(norbornyl-POSS) copolymers," Polym. Int. 49:453-457.

Jeong et al., (2000) "Shape memory polyurethane containing amorphous reversible phase," J. Mat.Sci. 35:1579-1583.

Kim et al. (2000) "Shape-Memory Behavior of Segmented Polyurethanes with an Amorphous Reversible Phase: The Effect of Block Length and Content," Journal of Polymer Science Part B: Polymer Physics 39:2652-2657.

Koopmans et al. (2003) "Polymer Refilling of Presbyopic Human Lenses In Vitro Restores the Ability to Undergo Accommodative Changes Invest," Ophthalmol. Vis. Sci. 44:250-257.

Lendlein et al. (2002), "Biodegradable, Elastic Shape-memory Polymers for Potential Biomedical Applications," Science 296(5537):1673-1676.

Lendlein et al. (2002) "Shape Memory Polymer," Angew. Chemie, International Edition 41:1973-2208.

Lendlein et al. (2002), "Shape-Memory Polymers," Angew.Chemie, International Edition 41:2034-2057.

Lendlein et al. (2001) "AB-polymer networks based on oligo(epsilon-caprolactone) segments showing shape memory properties," Proc. Nat. Acad. Sci. 98(3):842-847.

Li et al. (2002) "New Soybean Oil-Styrene-Divinylbenzene Thermosetting Copolymers. V.Shape memory effect," J. App. Pol. Sci. 84:1533-1543.

Li et al. (1999) "Shape memory effect of ethylene-vinyl acetate 25 copolymers," J. App. Poly. Sci. 71:1063-1070.

Li et al. (online Oct. 2007) "Thiourethane-based thiol-ene high Tg networks: Preparation, thermal, mechanical and physical properties," J. Polymer Science Part A: Polymer Chemistry 45(22):5103-5111.

Lin et al. (1998) "Study on Shape-Memory Behavior of Polyether-Based Polyurethanes. II. Influence of the Hard-Segment Content," J. App. Pol. Sci. 69:1563-1574.

Lin et al. (1998) "Study on Shape-Memory Behavior of Polyether-Based Polyurethanes. I. Influence of soft-segment molecular weight," J. App. Pol. Sci. 69:1575-1586.

Lin, J.R. (1999) "Shape-memorized crosslinked ester-type polyurethane and its mechanical viscoelastic model," J. Appl. Polym. Sci. 73:1305.

Liu et al. (online Mar. 2007) "Review of progress in shape-memory polymers," Journal of Materials Chemistry 17:1543-1558.

Liu et al. (2003) "Thermomechanical Recovery Couplings of Shape Memory Polymers in Flexure," Smart Materials & Structures, vol. 12, pp. 947-954.

Liu et al. (2003) "Shape memory polymers for medical applications," Adv. Mater. Process 161:31.

Liu et al. (2002) "Chemically cross-linked polycyclooctene: Synthesis, characterization, and shape memory behavior," Macromolecules 35(27):9868-9874.

Lu et al. (2005) "Investigations of Step-Growth Thiol-Ene Polymerizations for Novel Dental Restoratives," Dental Materials 21:1129-1136.

Maitland et al. (2002) "Photothermal properties of shape memory polymer micro-actuators for treating stroke," Las. Surg. Med. 30(1):1-11.

Metzger et al. (2002) "Mechanical properties of mechanical actuator for treating ischemic stroke," Biomed. Microdevices 4(2):89-96.

Morgan et al. (1977) Thiol-Ene photo-curable polymers, J Polym Sci-Polym Chem 15:627-645.

Nair et al. (2010) "Photopolymerized Thiol-Ene Systems as Shape Memory Polymers," Polymer 51(19):4383-4389.

Nuttelman et al. (Feb. 2009) "Macromolecular Monomers for the Synthesis of Hydrogel Niches and Their Application in Cell Encapsulation and Tissue Engineering," Prob. Polym Sci., 33(2):167-179.

Pan et al. (May 2008) "The glass transition temperature of polyurethane shape memory polymer reinforced with treated/non-treated attapoulgite (playgorskite) clay in dry and wet conditions," Smart Mater. Struct. 17, 045007.

(56) References Cited

OTHER PUBLICATIONS

Senyurt et al. (Mar. 2007) "Thermal and Mechanical Properties of Cross-linked Photopolymers Based on Multifunctional Thiol-Urethane Ene Monomers," Macromolecules 2007 40(9):3174-3182.
Sillion, B. (2002) "Shape memory polymers," Act. Chimique 3:182-188.
Takahashi et al. (1996) "Structure and Properties of Shape Memory Polyurethane Block Copolymers," Journal of Applied Polymer Science 60(7):1061-1069.
Wei et al. (Jan. 2007) "Photopolymerization of Ternary Thiol-Ene/Acrylate Systems: Film and Network Properties," J. Polym. Sci. A, Polymer Chem. 45:822-829.
Wei et al. (Nov. 2007), "Thiol-Ene Free-Radical and Vinyl Ether Cationic Hybrid Photopolymerization," Macromolecules 40(24):8788-8793.
Yakacki et al. (May 2007), "Unconstrained recovery characterization of shape-memory polymer networks for cardiovascular applications," J. Biomaterials 28:255-2263.
Yakacki, CM (2004) "Optimizing the Thermomechanics of Shape-Memory Polymers for Biomedical Applications," MRS Proceedings, 855, W3.27 doi:10.1557/PROC-855-W3.27.
Yan988g et al. (online Dec. 2008) "Newly UV-curable polyurethane coatings prepared by multifunctional thiol-and ene-termination polyurethane aqueous dispersions mixtures: Preparation and characterization," Polymer 50(7):1717-1722.
Zhang et al. (online Jan. 2007) "Novel Interpenetrating Networks with Shape-Memory Properties," J. Polym. Sci. A 45(5):768.
Zhu et al. (2003) "Shape-memory effects of radiation crosslinked poly(epsiloncaprolactone)," J. App. Poly. Sci. 90:1589-1595.
Extended European Search Report for European Application 09735620.8 mailed Nov. 8, 2013.

* cited by examiner

THIOL-VINYL AND THIOL-YNE SYSTEMS FOR SHAPE MEMORY POLYMERS

STATEMENT REGARDING FEDERALLY SPONSORED RESEARCH OR DEVELOPMENT

This invention was made with government support under Grant No. 0626023 awarded by the National Science Foundation and Grants Nos. 5F32DE015906 and EB004481 awarded by the National Institutes of Health. The United States Government has certain rights in the invention.

CROSS-REFERENCE TO RELATED APPLICATIONS

This application is a U.S. National Stage of International Application PCT/US2009/041359, filed Apr. 22, 2009, which designates the U.S. and which was filed in English and which claims the benefit of U.S. Provisional Application No. 61/047,026, filed Apr. 22, 2008. Each of these applications is incorporated by reference herein in its entirety.

BACKGROUND OF THE INVENTION

Shape memory materials are defined by their capacity to recover a predetermined shape after significant mechanical deformation (K. Otsuka and C. M. Wayman, "Shape Memory Materials" New York: Cambridge University Press, 1998). The shape memory effect is typically initiated by a change in temperature and has been observed in metals, ceramics, and polymers. From a macroscopic point of view, the shape memory effect in polymers differs from ceramics and metals due to the lower stresses and larger recoverable strains achieved in polymers.

The basic thermomechanical response of shape memory polymer (SMP) materials is defined by four critical temperatures. The glass transition temperature, $T_g$, is typically represented by a transition in modulus-temperature space and can be used as a reference point to normalize temperature for some SMP systems. The melting temperature may also be a relevant transition temperature for some systems. SMPs offer the ability to vary $T_g$ over a temperature range of several hundred degrees by control of chemistry or structure. The predeformation temperature, $T_d$, is the temperature at which the polymer is deformed into its temporary shape. Depending on the required stress and strain level, the initial deformation $T_d$ can occur above or below $T_g$ (Y. Liu, K. Gall, M. L. Dunn, and P. McCluskey, "Thermomechanical Recovery Couplings of Shape Memory Polymers in Flexure." *Smart Materials & Structures*, vol. 12, pp. 947-954, 2003). The storage temperature, $T_s$, represents the temperature in which no shape recovery occurs and is equal to or below $T_d$. The storage temperature $T_s$ is typically less than the glass transition temperature $T_g$. At the recovery temperature, $T_r$, the shape memory effect is activated, which causes the material to substantially recover its original shape, and is typically in the vicinity of $T_g$. Recovery can be accomplished isothermally by heating to a fixed $T_r$ and then holding, or by continued heating up to and past $T_r$. From a macroscopic viewpoint, a polymer will demonstrate a useful shape memory effect if it possesses a distinct and significant glass transition (B. Sillion, "Shape memory polymers," *Act. Chimique.*, vol. 3, pp. 182-188, 2002), a modulus-temperature plateau in the rubbery state (C. D. Liu, S. B. Chun, P. T. Mather, L. Zheng, E. H. Haley, and E. B. Coughlin, "Chemically cross-linked polycyclooctene: Synthesis, characterization, and shape memory behavior." *Macromolecules*. vol. 35, no. 27, pp. 9868-9874, 2002), and a large difference between the maximum achievable strain, $\epsilon_{max}$, during deformation and permanent plastic strain after recovery, $\epsilon_p$ (F. Li, R. C. Larock, "New Soybean Oil-Styrene-Divinylbenzene Thermosetting Copolymers. V. Shape memory effect." *J. App. Pol. Sci.*, vol. 84, pp. 1533-1543, 2002). The difference $\epsilon_{max}-\epsilon_p$ is defined as the recoverable strain, $\epsilon_{recover}$, while the recovery ration is defined as $\epsilon_{recover}/\epsilon_{max}$.

The microscopic mechanism responsible for shape memory in polymers depends on both chemistry and structure (T. Takahashi, N. Hayashi, and S. Hayashi, "Structure and properties of shape memory polyurethane block copolymers." *J. App. Pol. Sci.*, vol. 60, pp. 1061-1069, 1996; J. R. Lin and L. W. Chen, "Study on Shape-Memory Behavior of Polyether-Based Polyurethanes. II. Influence of the Hard-Segment Content." *J. App. Pol. Sci.*, vol. 69, pp. 1563-1574, 1998; J. R. Lin and L. W. Chen, "Study on Shape-Memory Behavior of Polyether-Based Polyurethanes. I. Influence of soft-segment molecular weight." *J. App. Pol. Sci.*, vol 69, pp. 1575-1586, 1998; F. Li, W. Zhu, X. Zhang, C. Zhao, and M. Xu, "Shape memory effect of ethylene-vinyl acetate copolymers." *J. App. Poly. Sci.*, vol. 71, pp. 1063-1070, 1999; H. G. Jeon, P. T. Mather, and T. S. Haddad, "Shape memory and nanostructure in poly(norbornyl-POSS) copolymers." *Polym. Int.*, vol. 49, pp. 453-457, 2000; H. M. Jeong, S. Y. Lee, and B. K. Kim, "Shape memory polyurethane containing amorphous reversible phase." *J. Mat. Sci.*, vol. 35, pp. 1579-1583, 2000; A. Lendlein, A. M. Schmidt, and R. Langer, "AB-polymer networks based on oligo(epsilon-caprolactone) segments showing shape-memory properties." *Proc. Nat. Acad. Sci.*, vol. 98, no. 3, pp. 842-847, 2001; G. Zhu, G. Liang, Q. Xu, and Q. Yu, "Shape-memory effects of radiation crosslinked poly(epsilon-caprolactone)." *J. App. Poly. Sci.*, vol. 90, pp. 1589-1595, 2003). One driving force for shape recovery in polymers is the low conformational entropy state created and subsequently frozen during the thermomechanical cycle (C. D. Liu, S. B. Chun, P. T. Mather, L. Zheng, E. H. Haley, and E. B. Coughlin, "Chemically cross-linked polycyclooctene: Synthesis, characterization, and shape memory behavior." *Macromolecules*. Vol. 35, no. 27., pp. 9868-9874, 2002). If the polymer is deformed into its temporary shape at a temperature below $T_g$, or at a temperature where some of the hard polymer regions are below $T_g$, then internal energy restoring forces will also contribute to shape recovery. In either case, to achieve shape memory properties, the polymer must have some degree of chemical crosslinking to form a "memorable" network or must contain a finite fraction of hard regions serving as physical crosslinks.

SMPs are processed in a manner that is termed programming, whereby the polymer is deformed and set into a temporary shape. A. Lendlein, S. Kelch, "Shape Memory Polymer," *Advanced Chemie, International Edition*, 41, pp. 1973-2208, 2002. When exposed to an appropriate stimulus, the SMP substantially reverts back to its permanent shape from the temporary shape. The stimulus may be, for example, temperature, magnetic field, water, or light, depending on the initial monomer systems.

The information included in this Background section of the specification, including any references cited herein and any description or discussion thereof, is included for technical reference purposes only and is not to be regarded subject matter by which the scope of the invention is to be bound.

BRIEF SUMMARY OF THE INVENTION

In one aspect, the invention provides medical devices for use in vivo, the devices comprising a thiol-vinyl, thiol-ene or thiol-yne shape memory polymer (SMP). The original molded shape of the SMP medical devices of the present invention can be deformed or crushed into a temporary shape having a reduced profile to facilitate insertion into a vessel, lumen, or other aperture or cavity. After insertion, the device can self-expand to assume a deployed configuration. The medical device may assume its deployed configuration due to changes in temperature, hydration, changes in other physiological conditions or combinations thereof. In an embodiment, these SMP devices are capable of exhibiting shape memory behavior at physiological temperatures and may be used in surgical procedures.

In an embodiment, the invention provides a medical device for in vivo medical applications comprising a shape memory polymer formed by polymerization of a mixture comprising:

a first monomer or oligomer comprising at least one aliphatic carbon-carbon double bond or at least one aliphatic carbon-carbon triple bond; and a second monomer or oligomer comprising at least one thiol group;

Two or more monomers or oligomers may be present in the mixture. At least one of the monomers or oligomers in the mixture may further comprise at least one urethane or thiourethane group. The glass transition temperature of the polymer may be from 15° C. to 50° C.

In another embodiment, the invention provides a medical device comprising a shape memory polymer formed by polymerization of a mixture comprising a first monomer or oligomer comprising at least one aliphatic carbon-carbon double bond or at least one aliphatic carbon-carbon triple bond, a second monomer or oligomer comprising at least one thiol group, and a third monomer or oligomer comprising at least one aliphatic carbon-carbon double bond. Three or more monomers or oligomers may be present in the mixture. At least one of the monomers or oligomers in the mixture may further comprise at least one urethane or thiourethane group. The glass transition temperature of the polymer may be from 15° C. to 50° C.

Hydrogen bonding between urethane groups and/or thiourethane groups can enhance the toughness of the polymer. In another embodiment, monomers or oligomers of useful thiol-ene or thiol-yne systems may comprise a functional group other than urethane group which is capable of providing hydrogen bonding capability or any other forms of intermolecular interactions such as pi-pi stacking that enhance the toughness of the polymer.

Thiol-vinyl photopolymerizations exhibit several unique characteristics relative to other radical polymerization systems. Thiol-vinyl systems exhibit nearly all of the advantages of typical photopolymerizations in that they polymerize rapidly, do not require solvents for processing, are optically clear, and have an excellent range of mechanical properties. In addition, thiol-vinyl polymerizations exhibit step growth polymerization and delayed gelation, have low volume shrinkage and stress, and enable radical polymerization of a wide range of thiol and vinyl functional group chemistries. Furthermore, thiol-vinyl systems have the advantage of being relatively uninhibited by oxygen, which can facilitate polymerization of thin sections.

In some embodiment, thiol-vinyl, thiol-ene or thiol-yne SMP polymers suitable for use with the invention have a glass transition temperature from 15° C. to 50° C. In other embodiments, the glass transition temperature can be from 20° C. to 50° C., 15° C. to 45° C., 25° C. to 50° C., from 25° C. to 40° C., from 30° C. to 50° C., or from 30° C. to 40° C.

In an embodiment, the devices of the invention maintain substantial shape fixity over the life of the implant or the patient. In different embodiments, the difference between the diameter (or some other characteristic dimension) of the freely deployed/expanded device and the initial diameter (or other characteristic dimension) of the device, divided by the initial diameter, is from 90% to 110% or from 95% to 105%.

In different embodiments, the expansion ratio of the devices of the invention are greater than 20%, greater than 50%, or greater than 100%.

In an embodiment, the SMP devices of the invention are sufficiently bio-durable to withstand exposure to the metabolism's biological processes and environment when placed in situ. The desired lifetime of the device may depend on its intended use. In an embodiment, the medical devices comprising the SMP are not degradable in storage and are not biodegradable over the lifetime of the implant or patient. In different embodiments, the thiol-vinyl, thiol-ene or thiol-yne shape memory polymer is not biodegradable within one year, within two years, within three years, within four years, within five years, within seven years, within 10 years, or within 15 years. In another embodiment, the thiol-vinyl, thiol-ene or thiol-yne shape memory polymer is biodegradable.

The medical devices of the invention may take a variety of forms. In an embodiment, the medical device is an endoprosthesis. In another embodiment, the medical device is an endoluminal device.

In another aspect, the invention provides methods for making medical devices comprising a thiol-vinyl, thiol-ene or thiol-yne shape memory polymer.

In an embodiment, the invention provides a method for making a shape memory polymer device comprising the steps of: preparing a mixture comprising: a first monomer or oligomer comprising at least one aliphatic carbon-carbon double bond or at least one aliphatic carbon-carbon triple bond; a second monomer or oligomer comprising at least one thiol group and a photoinitiator; forming the mixture; and exposing the mixture to light, thereby photopolymerizing the mixture.

In an embodiment, the invention provides a method for making an expandable shape memory polymer device comprising the steps of:

forming a medical device of the present invention into a first configuration (initial configuration);

deforming the device into a second configuration (storage configuration) at a temperature greater than or equal to $T_g$;

cooling the device to a storage temperature $T_s < T_g$ while maintaining the device in the second configuration;

wherein the device assumes a third configuration (deployment configuration) when heated to $T_g$ or above without mechanical constraint.

DETAILED DESCRIPTION OF THE INVENTION

Figure 1:
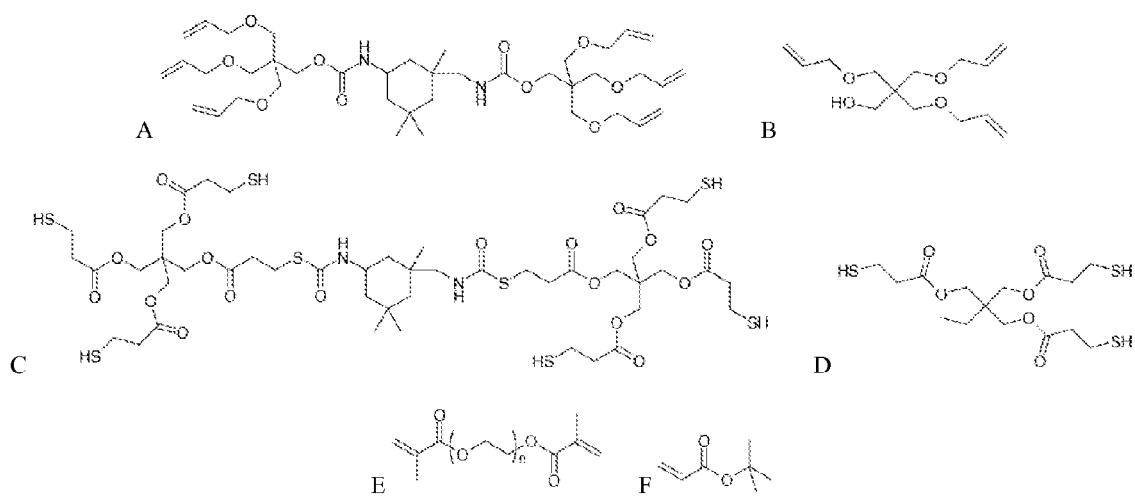
FIG. 1. Monomers used for Example 1: A) isophorone diurethane-6-allyl ether (IPDU6AE); B) allyl pentaerythritol (APE); C) isophorone diurethane thiol (IPDUTh); D) trimethylolpropane tris(3-mercaptopropionate) (TMPTMP); E) diethylene glycol dimethacrylate (DEGDMA, n=2) and poly (ethylene glycol 575) dimethacrylate (PEGDMA, n=13); F) tert-butyl acrylate (tBA).

The SMP systems of the invention are capable of assuming a memory/permanent shape at specific temperatures, and may be used to form biomedical devices. In an implementation, the SMP system may be biodegradable on demand. In another implementation, the SMP system may exhibit intermediate yet discrete stages of storage or permanent shape such that activating the material to one present temperature deploys the SMP material to one preset configuration and temperature change to another preset value deploys the SMP material to a second preset configuration. In yet another implementation, the SMP system may exhibit continuous deformation properties with temperature such that the material deploys continuously into a series of shapes based on a change in temperature.

As used herein, a thiol-vinyl system includes molecules containing one or more thiol functional groups, which terminate with —SH, and molecules containing one or more vinyl functional groups, which contain one or more carbon-carbon double bonds. The vinyl functional groups in the system may be provided by, for example, allyl ethers, vinyl ethers, norborenes, acrylates, methacrylates, acrylamides or other monomers containing vinyl groups. In some implementations, additional fillers, molecules, and functional groups may be provided to tailor and provide additional properties. In different embodiments, the thiol-ene system has about 1-90% of its functional groups as thiol functional groups or 2%-65% thiol functional groups. The balance of the functional groups (35% to 98% of the functional groups may be vinyl functional groups.

In an embodiment, 5-60 mol % of the functional groups in the system may be thiol functional groups and 95-40 mol % vinyl functional groups. In the present invention, the system of molecules containing thiol functional groups and the molecules forming vinyl functional groups is capable of forming a network.

In one class of thiol-vinyl systems, the vinyl monomer is not readily homopolymerizable and is termed an ene monomer. In these systems, the polymerization proceeds via a radically initiated step growth reaction between multifunctional thiol and ene monomers. The reaction proceeds sequentially, via propagation of a thiyl radical through a vinyl functional group. This reaction is followed by a chain transfer of a hydrogen radical from the thiol which regenerates the thiyl radical. The process then cycles many times for each radical generated in the photoinitiation step. This successive propagation/chain transfer mechanism is the basis for thiol-ene polymerization and is shown below.

step 1

Propagation

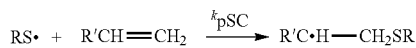

step 2

Chain Transfer

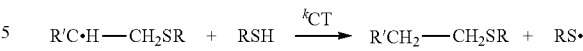

Because of the step growth mechanism of the polymerization, when the vinyl monomer is not homopolymerizable and no other homopolymerizable vinyl monomer are present, approximately equal amounts of initial functional groups (i.e., about 50% thiol functional groups and about 50% vinyl functional groups or a ratio of thiol to vinyl groups of 1:1) can allow highest conversion to be achieved. In different embodiments, the molar ratio of thiol groups may be from 30-70%, 40-60%, or 45-55% and the molar ratio of vinyl groups from 70%-30%, 60-40%, or 55-45%.

In the case where the vinyl monomer is also homopolymerizable such as, for example, acrylates, methacrylates, vinyl ester, acrylamide and the like, the polymerization includes a homopolymerization step, shown below.

step 3

Homopolymerization

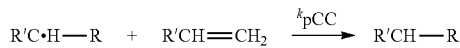

In an embodiment, the thiol-vinyl stem can include thiol groups, vinyl groups in non-homopolymerizable monomers or oligomers and vinyl groups in homopolymerizable monomers or oligomers. In an embodiment, the thiol groups and non-homopolymerizable vinyl groups together may constitute from 5 mol % up to, but not including 100 mol % of the thiol and vinyl groups, while the homopolymerizable groups may constitute from 95 mol % down to, but not including 0 mol %. In an embodiment the thiol groups and non-homopolymerizable vinyl groups together may constitute greater than 30 mol % of the mixture.

Thiol bearing monomers suitable for implementations of thiol-vinyl shape memory polymer systems include any monomer or oligomer having thiol (mercaptan or "SH") functional groups. Thiols are any of various organic compounds or inorganic compounds having the general formula RSH which are analogous to alcohols but in which sulfur replaces the oxygen of the hydroxyl group. Suitable monomers or oligomers may have one or more functional thiol groups. In an embodiment, the monomer or oligomer cannot be considered a polymer in its own right. In different embodiments, the monomer or oligomer has an average molecular weight less than 10,000, less than 5,000, less than 2,500, less than 1000, less than 500, from 200 to 500, from 200-1000, from 200-1, 500, from 200-2000, from 200-2,500, from 200-5000, or from 200-10,000. In different embodiments, the monomer or oligomer has at least two thiol functional groups, at least three thiol functional groups, at least four thiol functional groups, at least five thiol functional groups, at least six thiol functional groups or from 2 to 4 thiol functional groups.

Examples of suitable thiol bearing monomers include: pentaerythritol tetra(3-mercaptopropionate) (PETMP); trimethylolpropane tris(3-mercaptopropionate) (TMPTMP); glycol dimercaptopropionate (GDMP); IPDU6Th; and 1,6-hexanedithiol (HDTT), and benzene diol. Exemplary thiol bearing monomers are shown in Table 1.

TABLE 1

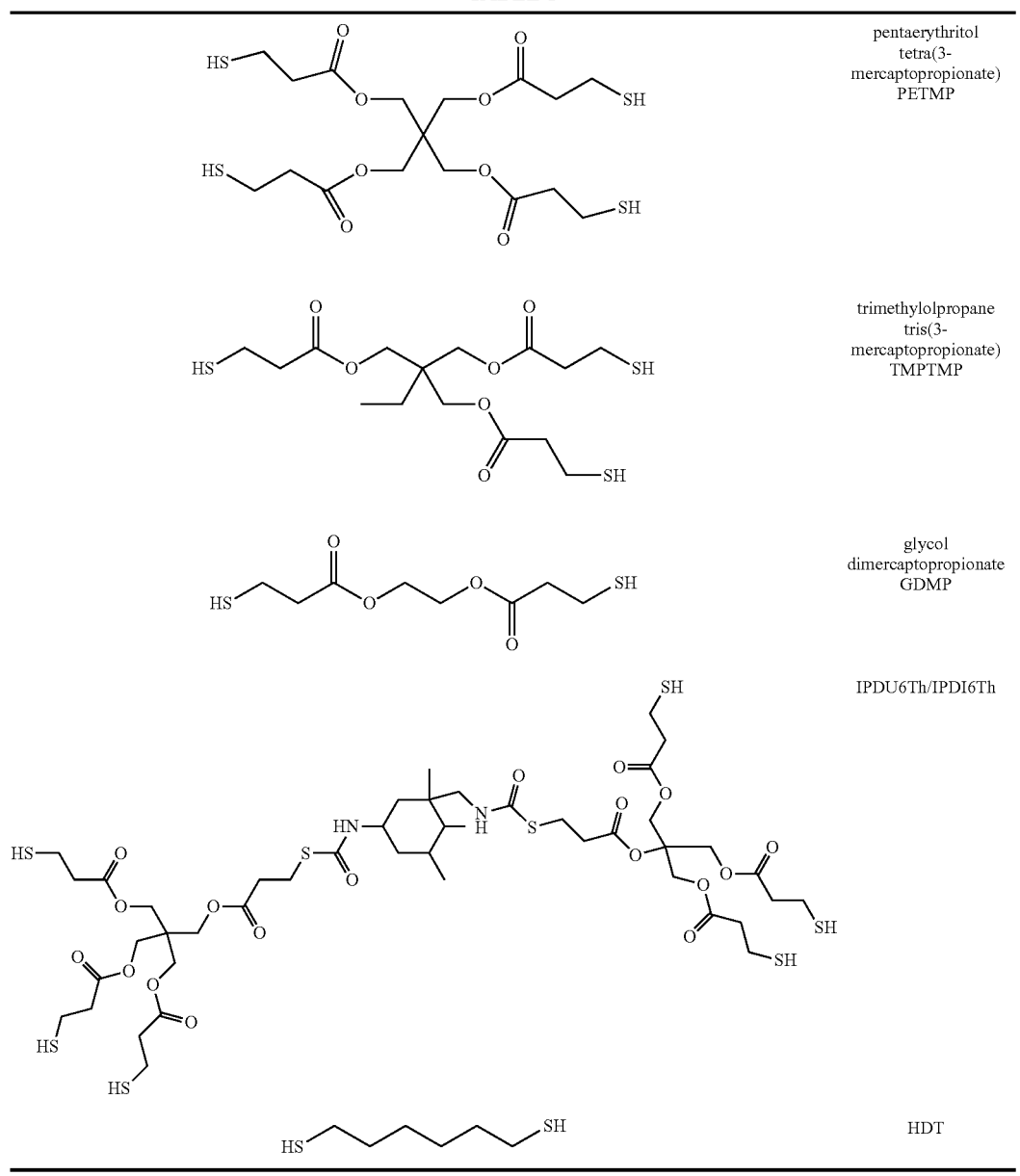

| | |
|---|---|
| | pentaerythritol tetra(3-mercaptopropionate) PETMP |
| | trimethylolpropane tris(3-mercaptopropionate) TMPTMP |
| | glycol dimercaptopropionate GDMP |
| | IPDU6Th/IPDI6Th |
| | HDT |

In an embodiment, the monomer or oligomer comprising a thiol group further comprises at least one thiourethane group. In an embodiment, the monomer comprises from 2-4 or 2-6 thiourethane groups. In an embodiment, the oligomer comprises from 4-40 thiourethane groups. A monomer or oligomer comprising thiourethane groups may be formed by reacting a polyisocyanate with a molecule comprising at least three thiol groups. For example, a diisocyante could be reacted with a trithiol or tetrathiol. In an embodiment, for example, the second monomer is a mixture of the reaction products of 2 equivalents of pentaerythritol tetra(3-mercaptopropionate) to 1 equivalent of isophorone diisocyanate. An exemplary synthesis method is described in Example 1. Suitable polyisocyanate molecules include, but are not limited to those shown in Table 2:

TABLE 2

| Toluene diisocyanate (2,4 isomer) | 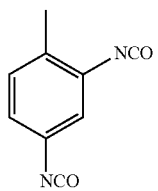 |
|---|---|

TABLE 2-continued

| Compound | Structure |
|---|---|
| Toluene diisocyanate (2,6 isomer) | 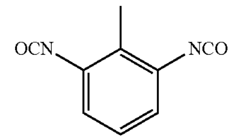 |
| Diphenylmethane 4,4'-diisocyanate | 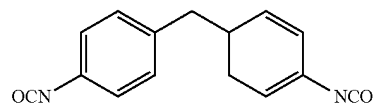 |
| Diphenylmethane 2,4'-diisocyanate | 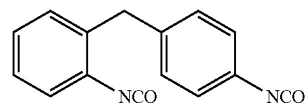 |
| Hexamethylene diisocyanate | 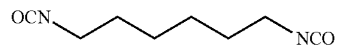 |
| Bis(4-isocyanatocyclohexyl)methane | 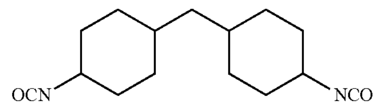 |
| Isophorone diisocyanate | 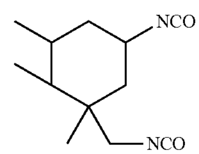 |
| Biuret of hexamethylene diisocyanate | 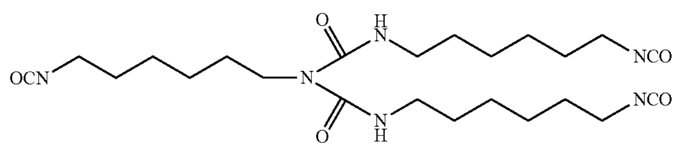 |
| Isocyanurate ring of hexamethylene diisocyanate | 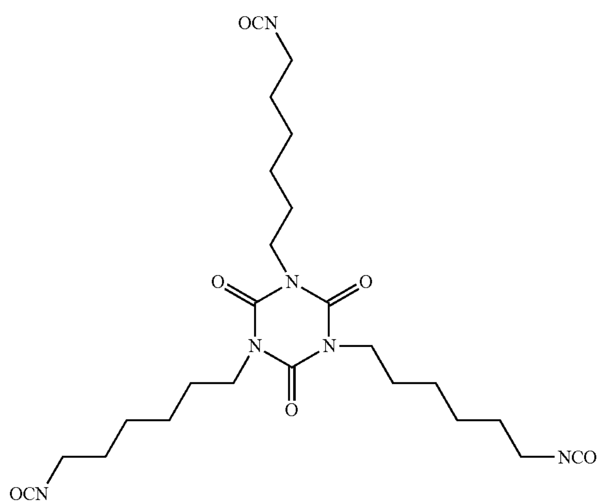 |

Monomers or oligomers having vinyl functional groups suitable for implementations of thiol-vinyl shape memory polymer systems include any monomer or oligomer having one or more functional vinyl groups, i.e., reaching "C═C" groups. In an embodiment, the monomer or oligomer cannot be considered a polymer in its own right. In different embodiments, the monomer or oligomer has an average molecular weight less than 10,000, less than 5,000, less than 2,500, less than 1000, less than 500, from 200 to 500, from 200-1000, from 200-1,500, from 200-2000, from 200-2,500, from 200-5000, or from 200-10,000. In different embodiments, the monomer or oligomer has at least two vinyl functional groups, at least three vinyl functional groups, at least four vinyl functional groups, at least five vinyl functional groups, at least six vinyl functional groups, or from 2 to 4 vinyl functional groups.

Examples of suitable vinyl monomers include: allyl pentaerythritol (APE); triallyl triazine trione (TATATO); trimethylolopropane diallyl ether (TMPDAE); hexanediol diacrylate (HDDA); trimethylolpropane triacrylate (TMPA); Ebecryl 8402; Vectomer 5015; and IPDU6AE. Exemplary vinyl bearing monomers are shown below.

TABLE 3

| Structure | Name |
|---|---|
| (structure) | allyl pentaerythritol APE |
| (structure) | triallyl triazine trione TATATO |
| (structure) | trimethylolpropane diallyl ether TMPDAE |
| (structure) | hexanediol diacrylate HDDA |
| (structure) | trimethylolpropane triacrylate TMPTA |
| (structure) | Ebecryl 8402 |
| (structure) | Vectomer 5015 |
| (structure) | IPDU6AE/ IPDI6AE |

Monomers or oligomers with acrylate or methacrylate functional groups may also be combined with thiol and/or vinyl monomers or oligomers. Exemplary acrylate and methacrylate monomers for use with thiol-vinyl shape memory polymer systems include tricyclodecane dimethanol diacrylate; tricyclodecane dimethanol dimethacrylate; bisphenol-A ethoxylated diacrylate; bisphenol-A ethoxylated dimethacrylate; bisphenol-A epoxy diacrylate; bisphenol-A epoxy dimethacrylate; urethane acrylates; urethane methacrylates; polyethylene glycol diacrylate; polyethylene glycol dimethacrylate and commercial monomers. Commercial monomers include aliphatic urethane acrylates such as Ebecryl 8402; Ebecryl 230; Loctite 3494; Ebecryl 4833; Ebecryl 3708.

In an embodiment, the monomer or oligomer comprising a vinyl group further comprises at least one urethane group. In an embodiment, the monomer comprises from 2-4 or 2-6 urethane groups. In an embodiment, the oligomer comprises from 4-40 urethane groups. A monomer comprising urethane groups may be formed by reacting a polyisocyanate with a molecule comprising an alcohol group and at least two vinyl groups. For example, a diisocyante could be reacted with a trimethylolpropane diallyl ether or allyl pentaerythritol. An exemplary synthesis method is described in Example 1 and in Reference 18. Suitable polyisocyanate molecules include, but are not limited to those shown in Table 2

Thiol-vinyl systems for shape memory polymers may also include and/or utilize various initiators, fillers, and accelerators, depending on the application. For example, if photopolymerization using visible light is desired, a commercially available photoinitiator such as Irgacure 819 or Irgacure 784 (manufactured by Ciba Specialty Chemicals Co. (http://www.cibasc.com)) may be used. If ultraviolet photopolymerization is desired, then 2,2-dimethyloxy-2-pheynlacetophenone (Irgacure 651, Ciba Specialty Chemicals Co.) may be used as an initiator or 1-hydroxy-cyclohexyl-phenyl-ketone (Irgacure 184, Ciba Specialty Chemicals).

As used herein, a thiol-yne system includes molecules containing one or more thiol functional groups, which terminate with —SH, and molecules containing one or more yne functional groups, which contain one or more carbon-carbon triple bonds. The functional groups in the system may be provided by, octadiyne or heptadiyne for example, or other monomers containing yne groups.

In another aspect, the invention provides thiol-vinyl polymer compositions suitable for use in medical devices.

In some embodiments, the combination of first and second, and optionally third, monomers or oligomers is selected to achieve a shape memory polymer having mechanical and physical properties useful for medical device functionality. In an embodiment, for example, the combination is a first monomer or oligomer having at least one urethane group and a second monomer or oligomer having at least one thiourethane group. In an embodiment, for example, the combination is a first monomer or oligomer having from 2-4 or 2-6 urethane groups and a second monomer or oligomer having from 2-4 or 2-6 thiourethane groups. In an embodiment, for example, the combination is a first monomer or oligomer having from 4-40 urethane groups and a second monomer or oligomer having from 4-40 thiourethane groups. In an embodiment, for example, the combination is a first monomer or oligomer selected from the group consisting of allyl pentaerythritol (APE), triallyl triazine trione (TATATO), trimethylolpropane diallyl ether (TMPDAE), hexanediol diacrylate (HDDA), trimethylolpropane triacrylate (TMPTA), Ebecryl 8402, Vectomer 5015 and IPDU6AE/IPDI6AE, and a second monomer or oligomer selected from the group consisting of pentaerythritol tetra(3-mercaptopropionate) (PETMP), trimethylolpropane tris(3-mercaptopropionate) (TMPTMP), glycol dimercaptopropionate (GDMP), IPDU6Th/IPDI6Th and HDT. As will be understood by those of skill in the art, the invention includes shape memory compositions, and devices thereof, formed by polymerization of all subcombinations of the monomers and oligomers disclosed herein.

In an embodiment, the invention provides a method of making a shape memory polymer device comprising the steps of preparing a monomer mixture, forming the mixture; and exposing the mixture to light, thereby photopolymerizing the mixture. Suitable methods for forming the mixture include, but are not limited to liquid casting, solution casting, melt processing, film extrusion, sheet extrusion, injection molding, compression molding, and blow molding. In an embodiment, the whole of the as-formed mixture is exposed to the light via flood cure or bulk cure. In another embodiment, the as-formed mixture is sequentially exposed to light so as to form a substantially homogeneous device. For example, the light exposure may be the same in each step or the light exposure may be adjusted between steps so that the shape memory polymer formed in each step has a similar network density or other physical property (for example, variation in the physical property less than 10% or less than 20%), such as transition temperature (e.g. $T_g$).

In different embodiments, the amount of functional group conversion is at least 30%, 40%, 50%, 60%, 70%, 80% or 90%.

In certain embodiments, the SMP segments can be natural or synthetic, although synthetic polymers are preferred.

In an embodiment, the thiol-vinyl, thiol-ene or thio-yne polymer is not biodegradable within the desired lifetime of the medical device. In another embodiment, the thiol-vinyl, thiol-ene or thio-yne polymer is not biodegradable within three years. In an embodiment, the non-biodegradable polymer does not include aromatic groups other than those present in naturally occurring amino acid. In an embodiment, the non-biodegradable polymer does not contain esters that are readily hydrolyzed at physiological pH and temperature.

In an embodiment, one or more of the monomers may be biodegradable. In general, biodegradable materials degrade by hydrolysis, by exposure to water or enzymes under physiological conditions, by surface erosion, by bulk erosion, or a combination thereof.

From a biomedical device perspective, there are characteristics that are considered favorable in device design. They are quantified in terms of stimuli (such as temperature) driven shape memory response, well-defined response temperature, modulus, and elongation.

The storage modulus of at least partially non-crystalline polymers decreases in the glass transition region. One method of determining the glass transition temperature is to use dynamic mechanical analysis (DMA) to determine the peak of the curve of tan δ (ratio of loss to storage modulus, $E''/E'$) as a function of temperature. The glass transition temperature determined by DMA is frequency dependent and generally increases with increasing frequency. In an embodiment, the measurement frequency is 1 Hz. The width of the tan δ peak is an indication of the breadth of the glass transition region. In different embodiments, the glass transition temperature of the SMP of the present invention (as determined from the peak of tan δ) is from 20° C. to 50° C., from 25° C. to 45° C., or from 30° C. to 40° C. In an embodiment, the glass transition temperature is in the specified ranges and the full width of the tan δ peak at half maximum is from 10-30° C. or from 10-20° C. Other methods of measuring the glass transition temperature include thermal mechanical analysis (TMA) and differential scanning calorimetry (DSC); TMA and DSC are heating rate dependent.

SMPs have significant capacity to change shape. SMP materials have the ability to activate with a mechanical force under the application of a stimulus. The stimulus may be light, heat, chemicals, or other types of energy or stimuli. The thermomechanical response of SMP materials can be controlled to predict and optimize shape-memory properties. Polymer systems may be designed and optimized to a high degree of tailorability that are capable of adapting and responding to patients' needs for biomedical applications such as orthopedic fixation, endolumenal applications, endovascular applications, closing wounds, repairing aneurisms, cosmetic surgery applications, etc.

More than one method may be used to design shape memory polymers for use in biomedical applications. In one method, the polymer transition temperature is tailored to allow recovery at the body temperature, $T_r \sim T_g \sim 37°$ C. (A. Lendlein and R. Langer, "Biodegradable, elastic shape-memory polymers for potential biomedical applications." Science, vol. 296, pp. 1673-1676, 2002). The distinct advantage of this approach is the utilization of the body's thermal energy to naturally activate the material. The disadvantage of this approach, for some applications, is that the mechanical properties (e.g., stiffness) of the material are strongly dependent on $T_g$, and can be difficult to alter in the device design process. In particular, it would be difficult to design an extremely stiff device when the polymer $T_g$ is close to the body temperature due to the compliant nature of the polymer. Another possible disadvantage is that the required storage temperature, $T_s$, of a shape memory polymer with $T_g \sim 37°$ C. will typically be below room temperature requiring "cold" storage prior to deployment.

In an alternative method, the recovery temperature is higher than the body temperature $T_r \sim T_g > 37°$ C. (M. F. Metzger, T. S. Wilson, D. Schumann, D. L. Matthews, and D. J. Maitland, "Mechanical properties of mechanical actuator for treating ischemic stroke," Biomed. Microdevices, vol. 4, no. 2, pp. 89-96, 2002; D. J. Maitland, M. F. Metzger, D. Schumann, A. Lee, T. S. Wilson, "Photothermal properties of shape memory polymer micro-actuators for treating stroke." Las. Surg. Med., vol. 30, no. 1, pp. 1-11, 2002). The advantage of the second method is that the storage temperature can be equal to room temperature facilitating easy storage of the device and avoiding unwanted deployments prior to use. The main disadvantage of the second method, for some applications, is the need to locally heat the polymer to induce recovery. Local damage to some tissues in the human body commences at temperatures approximately 5 degrees above the body temperature through a variety of mechanisms including apoptosis and protein denaturing. Advocates of the second approach use local heating bursts to minimize exposure to elevated temperatures and circumvent tissue damage. The use of one method over the other is a design decision that depends on the targeted body system and other device design constraints such as required in-vivo mechanical properties.

Any polymer that can recover an original shape from a temporary shape by application of a stimulus such as temperature is considered a SMP. The original shape is set by processing and the temporary shape is set by thermo-mechanical deformation. A SMP has the ability to recover large deformation upon heating.

A polymer is a SMP if the original shape of the polymer is recovered by heating it above a shape recovery temperature, or deformation temperature ($T_d$), even if the original molded shape of the polymer is destroyed mechanically at a lower temperature than $T_d$, or if the memorized shape is recoverable by application of another stimulus. Any polymer that can recover an original shape from a temporary shape by application of a stimulus such as temperature may be considered a SMP.

In an embodiment, the polymers are selected based on the desired glass transition temperature(s) (if at least one segment is amorphous) or the melting point(s) (if at least one segment is crystalline), which in turn is based on the desired application, taking into consideration the environment of use.

The preferred ranges of rubbery modulus can be different for different applications. The range of moduli of biological tissue can vary from 20 GPa (bone)[20] to 1 kPa (eye)[21].

In different embodiments, the recovery ratio of the SMPs employed in the biomedical devices of the invention is greater than 75%, 80%, 90%, 95%, from 80-100%, from 90-100%, or from 95-100%. In various embodiments, the maximum achievable strain is of the thiol-ene SMP from 10% to 800%, from 10% to 200%, from 10% to 500%, from 10% to 100%, from 20% to 800%, from 20% to 500%, from 20% to 800%. as measured at a temperature above the glass transition temperature. In different embodiments, the maximum achievable strain or strain to failure of the thiol-ene SMP is at least 30% at least 40%, at least 50%, at least 60%, or at least 70%, from 40% to 100%, from 40% to 60%, from 50% to 100%, from 60% to 100% as measured below the glass transition temperature. In different embodiments, the maximum achievable strain or strain to failure of the thiol-ene SMP is at least 30% at least 40%, at least 50%, at least 60%, or at least 70%, from 40% to 100%, from 40% to 60%, from 50% to 100%, from 60% to 100% as measured at ambient temperature (20-25° C.).

In general, the ability of the shape memory device to change conformation or configuration (e.g. to expand) is made possible by manufacturing a device having a first conformation or configuration (initial configuration) and, thereafter configuring the device into a second conformation or configuration (temporary or storage configuration), wherein this configuration is at least partially reversible upon the occurrence of a triggering event. After the triggering event, the device assumes a third configuration. In an embodiment, the third configuration (deployed configuration) is substantially similar to the first configuration. However, for an implanted medical device, the device may be constrained from assuming its initial shape (first configuration). In an embodiment, the device is capable of self-expansion to the desired dimensions under physiological conditions.

In an embodiment, the shape memory devices of the invention have shape fixity. In an embodiment, a shape memory device having shape fixity is able to achieve the original shape upon deployment, this original shape being substantially equivalent in dimensions to the dimensions of shape polymerized during the casting, molding or extrusion process used in manufacturing the device and before the device is deformed into its stored configuration. When mechanical deformation or constraint is present during or after deployment, a shape memory device having shape fixity returns to its original shape (original shape as defined above) upon release of the force causing the mechanical constraint or deformation. Such mechanical constraint or deformation may include, but is not limited to, constraint due to placement of the device into a catheter, trocar or other insertion tool used for minimally invasive delivery of a medical device, or deformation due to high blood flow, externally applied force, or force applied due to a surgical procedure.

In different embodiments, the difference between the diameter (or some other characteristic dimension) of the freely deployed/expanded device and the initial diameter (or other characteristic dimension) of the device, divided by the initial diameter (or other characteristic dimension), is from 80% to 120%, from 85%-115%, from 90% to 110% or from 95% to 105%. In an embodiment, the characteristic dimension may be the diameter or the width. For a coil, the characteristic dimension may be the inner or outer diameter of the coil. For a generally cylindrical stent, the characteristic dimension may be the inner or outer diameter of the stent. For a plug, the characteristic dimension may be the maximum width or diameter of the plug. In an embodiment, the initial characteristic dimension is measured at ambient temperature and the deployed configuration is measured at approximately body temperature (37° C.) or at 10° above $T_g$.

In an embodiment, the expansion ratio of a device of the invention refers to the percentage increase in diameter (or other characteristic dimension) of the device following conversion of the device from its temporary storage or delivery configuration to its deployed configuration. In an embodiment, the shape of the device may be similar in the delivery configuration and the deployed configuration (e.g. a disc) and the expansion may be greater than 20%, from 20% to 800%, from 20% to 50%, from 20% to 300%. Conversely, the compression ratio of the device refers to the percentage decrease in diameter of the device following deformation from its initial stage to its temporary state.

In another embodiment, the shape of the device may be substantially different in the delivery configuration and the deployed configuration, in which case the expansion ratio may refer to a percentage increase in the profile of the device. For example, the shape memory device may be a coil which is programmed to a linear device, with the profile of the device in the delivery configuration being the width or diameter of the linear device and the profile in the deployed configuration being the coil outer diameter.

In an embodiment, the medical device is an endoprosthesis. As used herein, "endoprosthesis" refers to any prosthetic device placed within the body. The term "endoluminal prosthesis refers to any prosthetic device placed within a lumen or duct of a body, where "lumen" refers to any cavity or passageway in the body.

In an embodiment, an endoluminal prosthesis may be used to partially or completely fill or block the lumen. In this embodiment, the endoluminal prosthesis may prevent flow of fluid or other material through the body lumen or duct. In this embodiment, the endoluminal prosthesis may be in the shape of a coil, plug, occluder, flap, and other form which partially or completely occludes the lumen. SMP plugs for occluding vessels, tubes, cavities and/or plugging septal defects may be formed in a variety of shapes and sizes and configurations. SMP plugs may be solid, hollow, or a combination thereof. SMP plugs may comprise a body portion and a tail portion, with the body portion being approximately oval-shaped or half-oval shaped. A number of SMP plug configurations are described in WO 2007/115208 (Shandas et al.).

In another embodiment, the endoluminal prosthesis may restore or enhance flow of fluids through the body lumen or duct. In this embodiment, the endoluminal prosthesis may be in the shape of a stent, coil, plugs with one more holes, or a valve. In an embodiment, the stent has a substantially cylindrical shape.

Thiol-vinyl polymerizations are not inhibited by oxygen to nearly the extent of acrylic systems and therefore allows in situ applications of these materials for use in biomedical applications. Exemplary applications of thiol-vinyl systems for shape memory polymers are presented below. In another implementation, the thiol-vinyl shape memory polymer material described above may be used for orthopedic applications. For example, the shape memory polymer material may be injected in a liquid or semi-soft gel form into an osseous space such as the medulla of a fractured long-bone, the facets or joints near small bones to facilitate small bone repairs, the cavity around the spinal cord for nucleus replacement techniques, or into a pre-drilled cavity or hole such as those used to repair natural or artificial ligaments into various joints such as the shoulder, knee, elbow, or hip. In these applications, the system may be configured to take on two or more different configurations, each configuration varying in mechanical property, biodegradability, and/or other features. In an implementation, the SMP system may be configured to be in a first state, which is a liquid or semi-soft gelatinous form. In this form, the SMP system may be injected using minimally invasive techniques such as a small-bore needle or catheter into the osseous space. The SMP system may be configured to polymerize using body heat or some external stimulus such as optical or ultrasound energy. The SMP system may then polymerize into a glassy configuration, the shape of which conforms to the local tissue anatomy. The polymerized SMP system may be capable of withstanding significant normal and shearing stresses, including the ability to create "lift" in areas such as inter-vertebral spaces.

In another implementation, a shape memory effect can be induced into the SMP system and programmed in situ as the SMP system polymerizes. For example, the system can be programmed to have a memory configuration slightly larger in one or more dimensions, but to initially be used in its "stored" configuration. The system may then be configured to deform into its memory configuration either abruptly or as with the application of an external stimulus such as optical energy or heat (delivered directly or using external techniques such as magnetic resonance or ultrasound), or gradually over time, the rate of which can be configured such that the deformation occurs over a period of a few hours or several months. This may be appropriate for use, for example, as a tissue expander.

In yet another implementation the system may be configured to degrade with time. The onset of degradation may be configured to occur upon the delivery of some external stimulus such as heat (delivered directly or indirectly using, for example, ultrasound or magnetic resonance), and/or light. Alternatively, the system may be configured such that the degradation begins at some preset time after deployment. The preset time may be, for example, days, weeks, or months.

After initiation of degradation, the system may also be configured such that the rate of degradation may be specified over time. Further, the system may be configured such that the rate of degradation varies over time.

Thiol-vinyl systems may also have the ability to co-polymerize with biological tissues such as ligaments, tendons, heart valves, decellularized tissue, components of engineered tissue such a collagen, elastin, and other structural protein scaffolds, and other tissue-scaffolds such as those used to seed stem cells. Thiol-vinyl systems may also be configured to facilitate the manufacture of composite materials including fabrics, metal, other shape memory alloys such as nickel titanium alloy, other metal alloys such as cobalt-chromium alloys, and other polymers including other shape memory polymers and hydrogels. Thiol-vinyl systems have the ability to co-polymerize with these materials while maintaining the necessary thermomechanical characteristics including glass transition temperature, width of the transition curve, and other features as noted above.

In still other implementations, thiol-vinyl systems may be used in a variety of cosmetic surgery applications where a need exists to inject a biocompatible material sub-cutaneously in a configuration such as a fluid or soft gel that can be easily moldable in situ. For example, one the correct shape is created, the shape may be "set" using an external stimulus such as heat, cold, or optical energy. The system may also be configured to include shape memory behavior that may be induced through the application of an additional stimulus such as thermal or optical energy. The system may be configured to degrade upon demand and/or degrade at a controlled rate, as discussed above. In yet another implementation, the system may be configured to encourage tissue ingrowth in polymer scaffolding, after which point the system may be adapted to degrade—partially or completely—after the elapse of a particular period of time or upon the application of a stimulus such as thermal or optical energy.

In certain embodiments, the medical device may be smooth in texture. In other embodiments, the medical device may range from smooth to fully textured. In alternative embodiments, the medical device may be partially textured.

A SMP material or network may include dissolving materials which may include part of the network or may be included in the formulation of the network before the network is polymerized (e.g., as an aggregate, mixed into the formulation). Dissolving materials may include materials that disperse over time, even if the material or part of the material does not actually dissolve or enter into a solution with a solvent. In other words, a dissolving material as used herein may be any material that may be broken down by an anticipated external environment of the polymer. In one embodiment, a dissolving material is a drug which elutes out of a SMP network. A dissolving material may be attached by chemical or physical bonds to the polymer network and may become disassociated with the polymer network over time.

Dissolving materials may be used to create surface roughness, for example, in order to increase biocompatibility of the network. In one embodiment, the dissolving material may initially form a part of the surface of the SMP network, and leave behind a rougher SMP surface after the dissolving material has dissolved. In another embodiment, the dissolving material may be placed within the body of the SMP network, and upon dissolving may create an impression in the surface of the SMP by allowing the SMP to collapse due to the dissolution of the dissolving material within the body of the SMP.

Dissolving materials, through their dissolution over time, may be used for many purposes. In one embodiment, the dissolution of a material may affect a dissolution or breaking up of a biomedical device over time. In another embodiment, the dissolution of a material may elute a drug, achieving a pharmacological purpose. Medications or drugs can be infused into biomedical device. In some embodiments medications or drugs may be coated onto surfaces of the biomedical device.

The matrix of the SMP-based material may be supplemented with a variety of drugs during the polymerization process or post-processing. For example, drugs to be added may include anti-inflammatory, pro-contraceptive, and anti-thrombotic drugs. These drugs can be added by injection into the liquid polymer before UV curing. Drugs may also be added to the SMP material post-polymerization using various surface modification techniques such as plasma deposition, for example.

An initial surface of an exemplary SMP material may be a rough surface. In one embodiment, an initial rough surface may include a dissolving material. In another embodiment, an initial rough surface may be created by including dissolving material inside a SMP network. Once the material has dissolved, a surface with a different roughness may be left behind. In one embodiment, a smooth surface is left after a dissolving material has dissolved. In another embodiment, a surface rougher than the initial is left behind after a dissolving material has dissolved. In another embodiment, a surface with a different type of roughness is left after a dissolving material has dissolved. For example, an initial surface may have roughness in a random pattern and a surface left after a dissolving material has dissolved may have a roughness that is ordered and repeating.

Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a compound or composition is claimed, it should be understood that compounds or compositions known in the art including the compounds or compositions disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods, and other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, a composition range or a mechanical property range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The preceding definitions are provided to clarify their specific use in the context of the invention.

The invention may be further understood by the following non-limiting examples.

Example 1

Materials

Diethylene glycol dimethacrylate (DEGDMA), poly(ethylene glycol 575) dimethacrylate (PEGDMA), and tert-butyl acrylate (tBA) were obtained from Sigma Aldrich. Allyl pentaerythritol (APE) was obtained from Perstorp, pentaerythritol tetra(3-mercaptopropionate) (PETMP) was obtained from Evans Chemetics, isophorone diisocyanate (IPDI) was obtained from Bayer, and the photoinitiator Irgacure 651 was obtained from Ciba Specialty Chemicals. Isophorone diurethane thiol (IPDUTh) was synthesized by mixing isophorone diurethane trimethylolpropane tri(3-mercaptopropionate) and 0.05 wt % dibutyl tin dilaurate as catalyst. The reaction will form a series of oligomers with the idealized product shown in FIG. 1. Isophorone diurethane 6-allyl ether (IPDU6AE) was synthesized from a reaction of isophorone diurethane and allyl pentaerythritol (APE). 0.5 wt % dibutyl tin dilaurate was used as the catalyst.

The monomers utilized in this study are shown in FIG. 1. Polymer Coil FabricationA mold for the fabrication of polymer coils consisted of a threaded Teflon cylinder inserted in a tight-fitting glass tube. Formulated resin was introduced into the mold and was photopolymerized in situ using a UV lamp (Black-Ray Model B100AP). After curing, the glass tube was broken and the polymer was removed from the mold.

Shape Memory Programming and Recovery

The coils were heated to 10° C. above their $T_g$ and programmed into their temporary shape by constraining them inside a straight glass tube. The polymer was cooled to −5° C. and maintained for one week in this extended geometry. The polymer was then removed from the tube, observed at room temperature and then placed in an oven maintained at 10° C. above the $T_g$ of the polymer. The time taken for the polymer to revert back into its original shape was recorded by visual observation.

Dynamic Mechanical Analysis (DMA)

DMA experiments were performed using a TA Instruments Q800 DMA.

Glass transition temperature ($T_g$) was determined from fully cured samples with dimensions 5×3.5×1 mm. Samples temperature was ramped at 3° C./min from −15 to 75° C. at a frequency of 1 Hz and a strain of 0.1% in tension. The $T_g$ was assigned as the temperature at the tan δ curve maximum. The $T_g$ width was determined as the full width of the tan δ curve at half the maximum height. The rubbery modulus values were determined at a temperature of $T_g$+25° C.

Free Strain Recovery was determined from fully cured samples with dimensions 20×5×1 mm. The polymers were held at a temperature 5° C. above the $T_g$ of the system and strained 10-20 percent (making sure to stay within the linear regime). While maintaining the strain, the polymers were cooled to −10° C. The force was then maintained at zero and the strain recovery was observed as the temperature was increased to 25° C. above the $T_g$ at the rate of 3° C.

Constrained Stress Recovery was determined from cylindrical samples measuring 9 mm in diameter and 9 mm in length. Samples were strained 10% at a rate of $1\times10^{-3}$ s$^{-1}$ at $T_g$. Samples were subsequently cooled to −10° C. and held for 30 minutes. Recovery stresses were recorded by maintaining a constant strain while heating the samples back up to $T_g$ at the rate of 2° C./min and then maintaining the samples at $T_g$ for 30 minutes.

Materials Testing System (MTS)

Tensile strength tests were conducted on a Instron Universal Testing Machine (Model 5565) equipped with an Instron SFL Temperature Controlled Chamber (Model 3119-405-21) and a temperature controller (Euro 2408). Dog bone shaped samples of dimensions 40×6.5×1 mm were used. The initial separation of the system was set at 30 mm and a crosshead speed of 3 mm/min was applied. Table 6 data (modulus and strain at break) were performed at ambient temperature (in the glassy regime).

Results and Discussion.

This work evaluates three different thiol-ene polymer systems in comparison with a control system. The polymer systems chosen for this study exhibited glass transition temperatures in the range of 30 to 35° C., making them suitable for thermally induced biomedical applications. The control polymer system was a previously examined shape memory polymer comprised of 49 wt % tert-butyl acrylate (tBA), 0.5 wt % diethylene glycol dimethacrylate (DEGDMA), and 49.5 wt % PEGDMA[refs] (tBA/PEGDMA). The first thiol-ene system we studied was polymerized from a stoichiometric mixture of two commercially available thiol and ene monomers, trimethylolpropane tris(3-mercaptopropionate) (PETMP) and allyl pentaerythritol (APE). The resulting polymer films exhibited a strong shape memory response. However, the polymer had a low elongation at break (20%) and glass transition temperature (6° C.) and was the samples made were extremely brittle, breaking easily during handling. Thiol-ene systems with higher $T_g$s and tensile strengths such as PETMP and triallyl triazine trione (TATATO) were also considered.

However, the PETMP/TATATO system exhibits a Tg much higher than body temperature (63° C.)[16]. To obtain thiol-ene systems with improved toughness and that had $T_g$s close to body temperature, we synthesized urethane based thiol and ene monomers. Polyurethanes impart improved toughness and increased $T_g$ to polymers and also have a history of use in shape memory polymers a record of proven biocompatibility[17]. Thiourethane-based thiol-ene (TUTE) polymer films have been shown to possess excellent physical and mechanical properties[18][19].

Figure 2:
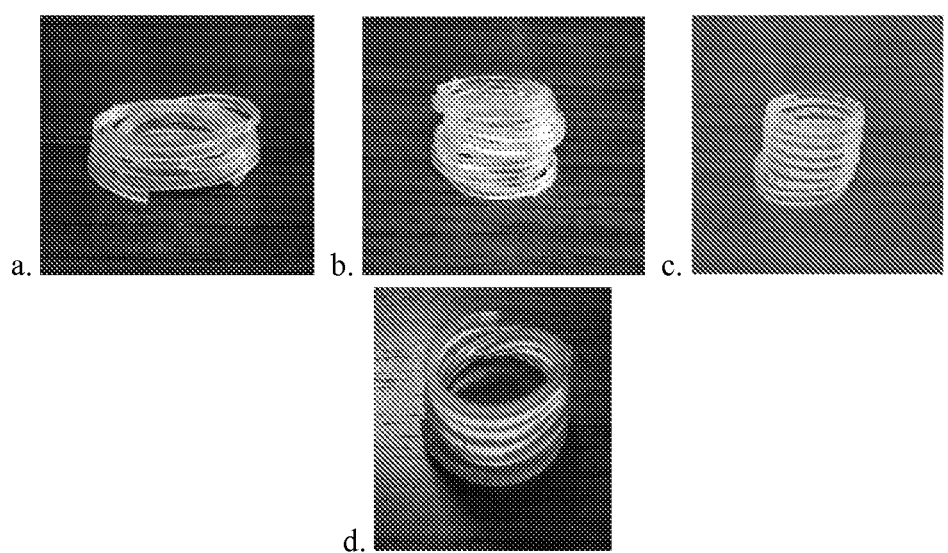
FIG. 2: Images of polymer coils after removal from the teflon mold; (a) tBA/PEGDMA, (b) TMPTMP/IPDI6AE, (c) IPDUT/APE and (d) IPDUT/IPDU6AE.
Figure 3:
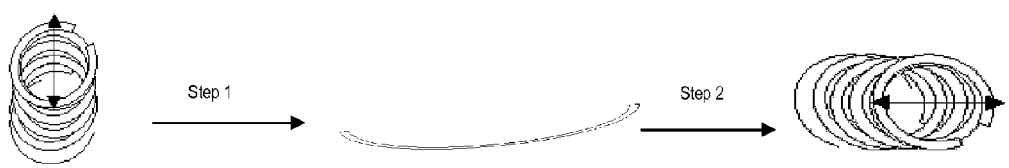
FIG. 3: Schematic of a programming process for a shape memory coil.
Figure 4:
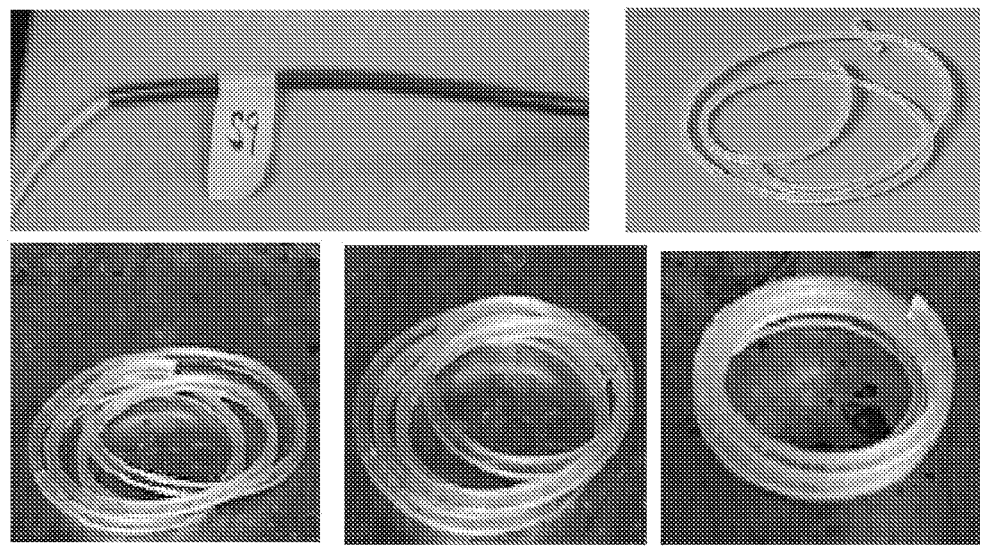
FIG. 4: The process followed to quantify shape memory behavior is outlined in the coil images of the IPDUT/APE polymer system. (a) The polymer coils are heated to 10° C. above their $T_g$ and then constrained in tubing. The polymers are then cooled below their $T_g$ to −5° C. (b) The polymers are released from the tubing at ambient temperature, whereby they were observed for 4 minutes. Polymers were then placed in an oven maintained at 10° C. above their $T_g$. The time taken for the coils to form was recorded. Coil images were recorded at (c) 4 minutes, (d) 4.5 minutes, and (e) 5 minutes.

Each of the polymer systems was examined for shape memory programming and shape retention. The results are tabulated in Table 4. A comparison of the coil diameter with the mold diameter is detailed to reflect the initial state of the polymer system. Images of polymers after removal from the Teflon mold are shown in FIG. 2. Subsequently, the polymers were programmed to their temporary shape and then thermally stimulated at 10° C. above their $T_g$ to regain their original shape. The coil diameter was again observed and the percent change from the mold diameter calculated. A schematic of this process is shown in FIG. 3. FIG. 4 depicts the procedure by which polymer coils are released from their constrained temporary shape at room temperature and subsequently heated to a temperature above their $T_g$. Ideal shape memory polymer systems will exhibit coil diameters closely resembling that of the mold both before and after programming. For biomedical applications such as cardiovascular stents, shape retention is extremely important to prevent leakage around the edges of the polymer. In comparison with the control tBA/PEGDMA system, the thiol-ene systems exhibit better mold retention both before and after programming and a more rapid shape memory response (by visual observation). Additionally, the thiol-ene systems exhibited excellent toughness as qualitatively determined by their ability to be handled and manipulated without breaking.

TABLE 4

Coil and mold diameter and percent resemblance to mold for shape memory polymers.

| Formulation | Mold Diameter (mm) | Initial Coil Diameter (mm) | Coil Diameter after Programming (mm) | Percent Resemblance to Mold |
|---|---|---|---|---|
| tBA/PEGDMA | 21.5 ± 1 | 25.2 ± 1 | 25.5 ± 2 | 118% |
| TMPTMP/IPDU6AE | 21.7 ± 1 | 21.7 ± 1 | 21.8 ± 1 | 100% |
| IPDUT/IPDU6AE | 21.5 ± 1 | 18.6 ± 2 | 21.8 ± 1 | 101% |
| IPDUT/APE | 21.7 ± 1 | 20.5 ± 1 | 21.1 ± 2 | 97% |

Figure 5:
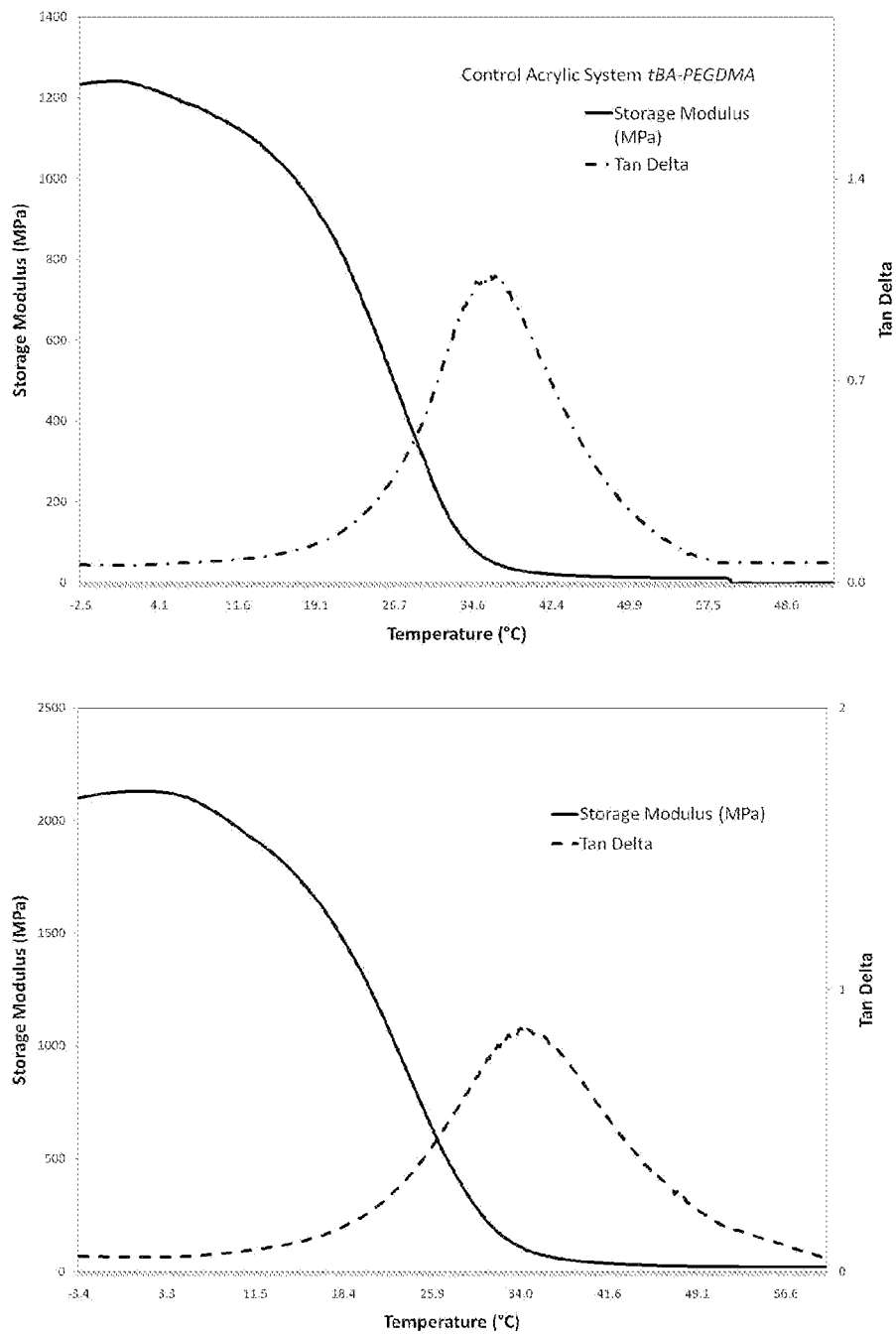
FIG. 5: storage modulus and tan δ versus temperature curves for the control shape memory polymer system and a representative thiol-ene system (IPDUT/APE) of Example 1.

Table 5 details the rubbery storage moduli and $T_g$ of the polymer systems evaluated in this study. Shown in FIG. 5 is a representative storage modulus and tan delta versus temperature curve of the control tBA/PEGDMA system and the IPDUT/APE system. The $T_g$ of the urethane thiol-ene polymer systems are comparable to that of the tBA/PEGDMA control. The rubbery moduli of the IPDUT/APE and the TMPTMP/IPDU6AE are both higher than the control and exhibit better mold retention than the tBA/PEGDMA system. However, the IPDUT/IPDU6AE system exhibits the lowest rubbery modulus while still exhibiting much better mold retention than the tBA/PEGDMA system.

TABLE 5

Rubbery moduli at $T_g$ + 25 C. and $T_g$s of the shape memory polymer systems.

| Formulation | Rubbery Modulus (MPa) | $T_g$ (° C.) |
|---|---|---|
| tBA/PEGDMA | 12 ± 1 | 35 ± 3 |
| PETMP/APE | 30 ± 3 | 7 ± 1 |
| IPDUT/APE | 19 ± 4 | 33 ± 3 |
| IPDUT/IPDU6AE | 7 ± 1 | 35 ± 3 |
| TMPTMP/IPDU6AE | 17 ± 3 | 34 ± 4 |

Table 6 details the polymer tensile modulus, peak load capacity, and strain at break of the polymer systems (at ambient temperature, in the glassy regime). The tensile tests showed that although the thiol-ene systems exhibited a uniformly strong shape memory response, there was significant variation in the modulus, peak load capacity and elongation of the polymers that did not show a correlation to the observed shape memory behavior. The range of moduli of biological tissue can vary from 20 GPa (bone)[20] to 1 kPa (eye)[21]. As the modulus values of biomedical implants and devices are normally engineered to match the immediate in vivo environment, surrounding the material, this test baselines the type of device for which a particular thiol-ene shape memory system could have a potential use.

TABLE 6

Modulus, peak load, and strain at break for each of the shape memory polymer systems studied.

| Formulation | Modulus (MPa) | Strain at Break (mm/mm) |
|---|---|---|
| PETMP/APE | 11.4 ± 0.3 | 0.2 ± 0.1 |
| tBA/PEGDMA | 9.3 ± 0.1 | 1.0 ± 0.2 |
| IPDUT/APE | 6.9 ± 0.1 | 0.7 ± 0.1 |
| IPDUT/IPDI6AE | 6.7 ± 0.2 | 1.0 ± 0.1 |
| TMPTMP/IPDU6AE | 11.5 ± 0.1 | 0.6 ± 0.3 |

TABLE 7

Free strain recovery percent, onset temperature, and transition width for each of the shape memory polymer systems.

| Formulation | Free Strain Recovery (%) | Strain Recovery Onset Temp (° C.) | Strain Recovery Transition Width (° C.) |
|---|---|---|---|
| tBA/PEGDMA | 100% | 20 ± 3 | 34 ± 4 |
| IPDUT/APE | 100% | 20 ± 2 | 28 ± 1 |
| IPDUT/IPDU6AE | 100% | 22 ± 1 | 38 ± 2 |
| TMPTMP/IPDU6AE | 100% | 23 ± 3 | 31 ± 3 |

Figure 6:
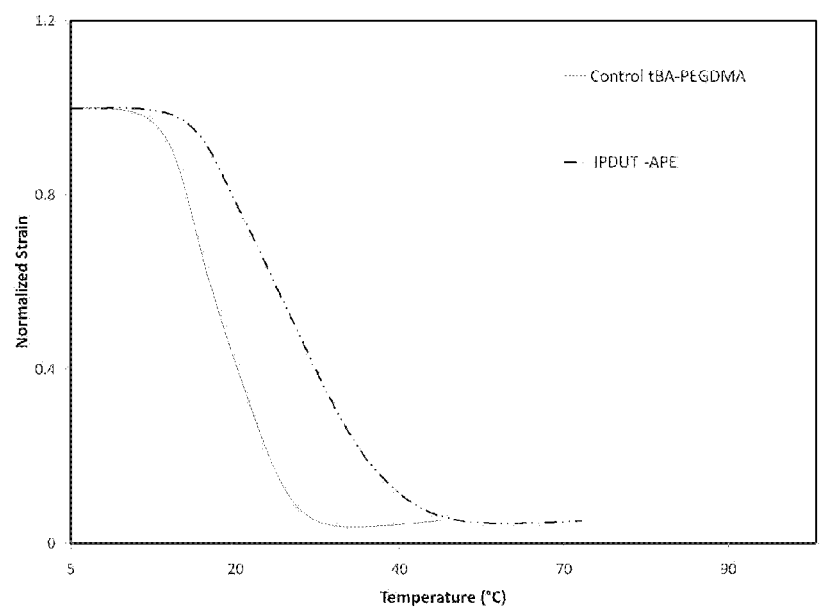
FIG. 6: Free strain recovery versus temperature for each of the shape memory polymer systems of Example 2.

Free-strain recovery can be measured in terms of unconstrained polymer shape change as a function of temperature during heating. The free-strain recovery results are shown in FIG. 6 and the data is tabulated in Table 7. All systems showed a 100% strain recovery with similar recovery onset temperatures and recovery transition widths.

Constrained-stress recovery is the stress generated by the shape memory polymer against external constraints while maintaining the polymer in a strained state during heating. Effectively, this is a measure of the stress that can be exerted by the shape memory polymer during actuation of the shape change from its temporary shape to permanent shape against an obstacle. The results show that all systems recovered completely from the imposed strain although constrained by the load. Again the results obtained here were comparable to those of the acrylic system.

Conclusion

This work demonstrates thiol-ene based shape memory systems with $T_g$s close to body temperature. We have base lined the shape memory response, thermomechanical, and mechanical properties of the thiol-ene systems in comparison with an acrylic control system. The thiol-ene polymer systems exhibit a rapid and distinct shape memory response with excellent shape retention by thermal stimulation. However, the quantified mechanical properties did not directly correlate to observed shape memory response in regards to actuation, mold retention, or toughness. The thiol-ene systems studied in this work demonstrate new shape memory polymer systems that exhibit excellent shape memory response and characteristics and that are tailorable to exhibit a wide range of polymer mechanical properties that are suitable for biomedical applications.

Example 2

Experimental work on the thiol-vinyl systems was performed to demonstrate the shape memory properties of the thiol-vinyl polymer systems. More specifically, the following monomer systems were studied, with a tBA/PEGDMA (t-butyl acrylate/polyethylene glycol dimethacrylate 770) control system and Ebecryl 4833, Ebecryl 3708, Ebecry 8402, and Loctite 3494 urethane acrylate control systems used as a comparison:

TABLE 8

System Compositions

| System | Composition wt % |
|---|---|
| Acrylate Control | |
| tBA/PEGDMA | 50/50 |
| Thiol-Ene | |
| TMPTMP/IPDI6AE | 52/48 |
| IPDUT/IPDI6AE | 65/35 |
| IPDUT/APE | 70/30 |
| PETMP/APE | 59/41 |
| GDMP/APE | 58/42 |
| Thiol-Acrylate | |
| TMPTMP/Loctite 3494 | 10/90 |
| GDMP/Loctite 3494 | 10/90 |
| Thiol-Ene-Acrylate | |
| GDMP/Vectomer 5015/Ebecryl 8402 | 12.5/17.5/70 |
| PETMP/APE/Ebecryl 8402 | 29.5/20.5/50 |
| GDMP/APE/Ebecryl 8402 | 17.4/12.6/70 |

TABLE 8-continued

System Compositions

| System | Composition wt % |
|---|---|
| TMPTMP/TATATO/Ebecryl 230 (1) | 18.5/11.5/70 |
| TMPTMP/TATATO/Ebecryl 230 (2) | 31/19/50 |
| Urethane Acrylate | |
| Ebecryl 4833 | 100 |
| Ebecryl 3708 | 100 |
| Ebecryl 8402 | 100 |
| Loctite 3494 | 100 |

Resins were formulated by thoroughly mixing each of the monomer systems described above in a glass vial with 1 wt % Irgacure 651 as a photoinitiator. Shape memory characteristics of the resulting polymers were determined using a specially designed system that consists of a Teflon mold and a glass tube to fix the polymer into its permanent shape. Threads were cut along the tubular mold and the monomer mixture was poured between the glass tube and the mold. A UV-Lamp (Model B100AP; Black-Ray) was used to photopolymerize each of the solutions in the mold. Images of the polymer coils after removal from the Teflon mold are shown in FIG. 2a-2c.

Once the polymer coils were removed from the Teflon mold, the diameters of the coils were measured. The coils were then exposed to a temperature above their glass transition temperature, $T_g$, and programmed into their temporary shape, which amounted to drawing them into a straight piece of wire contained inside of a tube. Each polymer was then constrained at −5° C. for one week in this extended geometry. After this period, each polymer was removed from its respective tube and placed in an oven maintained at 10° C. above the $T_g$ of the polymer. Visual observation was used to determine the amount of time required for each polymer to coil back into its original shape. This process is outlined in FIG. 4.

A comparison of the coil diameter with the mold diameter is detailed to reflect the initial state of the polymer system. Subsequently, the polymers were programmed to their temporary shape and then thermally stimulated to regain their original shape. The coil diameter was again observed and the percent change from the mold diameter was calculated. Additionally, the response time was recorded for the time taken for the coils to form when exposed to a temperature 10° C. above their glass transition temperature. The shape memory response of the polymers is presented below. (See, Table 9).

Ideal shape memory polymers will exhibit coil diameters closely resembling that of the mold both before and after programming. All of the thiol-vinyl systems and urethane acrylate polymer systems met this criteria. However, the response time and thermal stability performance below the thermal stimulus temperature was better for the thiol-vinyl systems than the acrylate systems.

TABLE 9

Shape Memory Response

| System | Mold Diameter (mm) | Initial Coil Diameter (mm) | Coil Diameter after Programming (mm) | Percent Resemblance to Mold | Shape Memory Response Time (s) |
|---|---|---|---|---|---|
| tBA/PEGDMA | 21.5 | 25.2 | 25.5 | 118 | 120 |
| TMPTMP/IPDI6AE | 21.7 | 21.7 | 21.8 | 100 | 60 |
| IPDUT/IPDI6AE | 21.5 | 18.6 | 21.8 | 101 | 50 |
| IPDUT/APE | 21.7 | 20.5 | 21.1 | 97 | 60 |
| Ebecryl 8402 | 21.5 | 20.0 | 21.2 | 99 | 95 |
| Loctite 3494 | 21.7 | 21.8 | 21.9 | 101 | 75 |

Fourier Transform Infrared (FTIR) Spectroscopy studies were conducted using a Nicolet 750 Magna FTIR spectrometer. Resin samples were placed between two glass slides separated with 1 mm spacers and the reaction was initiated via an EFOS Ultracure 100s Plus light source with a 320-500 nm filter. Irradiation intensities were measured with a Cole-Parmer instruments Co. series 9811 radiometer. The recorded series scans were measured with spectra taken at the rate of approximately two scans per second. Double bond conversion was monitored with the carbon-carbon double-bond absorption peak at ~6200 cm$^{-1}$. The results of the FTIR analysis are presented below (Table 10).

TABLE 10

Overall functional group conversion, cure time, and estimated leachable monomer %. All samples contain 1.0 wt % Irgacure 651 and were irradiated at 5 mW/cm$^2$. Thiol functional group conversion is assumed equivalent to vinyl conversion.

| System | Functional Group Conversion (%) | Time to Reach 90% of Final Conversion (s) | Leachable Monomer % |
|---|---|---|---|
| tBA/PEGDMA | 98 | 120 | 1.0 |
| TMPTMP/IPDI6AE | 86 | 30 | 0.1 |
| GDMP/Vectomer 5015/Ebecryl 8402 | 92 | 60 | 0.5 |
| TMPTMP/TATATO/Ebecryl 230 | 85 | 30 | 1.7 |
| TMPTMP/TATATO/Ebecryl 230 | 87 | 75 | 1.0 |
| Loctite 3494 | 94 | 105 | n/a |

The monomer conversion is important to estimate the leachable monomers remaining in the polymer after curing to determine biocompatibility.

Dynamic Mechanical Analysis (DMA) was performed on the same samples that were subject to FTIR. The sample size was made to a specification of 5×2.5×0.99 mm$^3$. Dynamic flexural temperature scans were run on samples of each polymer using a Perkin Elmer DMA-7 to obtain the glass transition temperature of the polymer. The tan delta curve or the loss tangent curve, which is the ratio of the loss modulus to the storage modulus, was recorded versus temperature. The glass transition temperature, $T_g$, was taken to be the maximum of the tan delta curve. The $T_g$ width was taken to be the full width of the tan delta curve at half the maximum height. Specimens were scanned over a temperature range from −65 to 100° C. with a ramping rate of 3° C./min in extension mode (sinusoidal stress of 1-Hz). The results of the DMA are presented below (Table 11).

TABLE 11

Glass transition temperature and glass transition temperature half width.

| System | $T_g$ (° C.) | $T_g$ width (° C.) |
|---|---|---|
| tBA/PEGDMA | 36 | 24 |
| TMPTMP/IPDI6AE | 34 | 25 |
| IPDUT/IPDI6AE | 40 | 30 |
| IPDUT/APE | 29 | 18 |
| PETMP/APE | 6 | 9 |
| GDMP/APE | −20 | — |
| GDMP/Vectomer5015 | 13 | — |
| PETMP/APE/Ebecryl 8402 | 8 | 11 |
| GDMP/APE/Ebecryl 8402 | −4 | — |
| TMPTMP/TATATO/Ebecryl 230 (1) | 8 | 11 |
| TMPTMP/TATATO/Ebecryl 230 (2) | −4 | — |
| Ebecryl 8402 | 40 | 31 |
| Loctite 3494 | 70 | 30 |

Materials testing system (MTS) tests to determine tensile strength were conducted on an MTS tensile test machine. Dog bone shaped samples of dimensions 40×6.35×0.99 mm$^3$ were used. The initial separation of the system was set at 30 mm at a crosshead speed of 3 mm/min. The results of the MTS tests are presented below. (See, Table 12)

TABLE 12

Polymer modulus, peak load, and strain at break.

| System Number | Modulus (MPa) | Peak Load (MPa) | Strain at Break (mm/mm) |
|---|---|---|---|
| tBA/PEGDMA | 12.0 | 43.5 | 0.96 |
| TMPTMP/IPDI6AE | 15.0 | 32.0 | 0.56 |
| IPDUT/IPDI6AE | 6.3 | 25.0 | 1.00 |
| IPDUT/APE | 7 | 59.0 | 0.77 |
| PETMP/APE | 11.8 | 9.3 | 0.16 |
| GDMP/APE | 2.9 | 3.8 | 0.25 |
| GDMP/Vectomer5015 | 15.0 | 32.0 | 0.56 |
| PETMP/APE/Ebecryl 8402 | 6.9 | 11.7 | 0.31 |
| GDMP/APE/Ebecryl 8402 | 2.5 | 4.6 | 0.36 |
| TMPTMP/TATATO/Ebecryl 230 (1) | 6.9 | 11.7 | 0.31 |
| TMPTMP/TATATO/Ebecryl 230 (2) | 2.5 | 4.6 | 0.36 |

The control polymer system for the analysis was a known shape memory polymer system comprised of t-butyl acrylate and polyethylene glycol (770) dimethacrylate (PEGDMA). Seventeen monomer resins were formulated and compared to the control. The systems were categorized as acrylate (control), thiol-ene, thiol-acrylate, thiol-ene-acrylate, urethane thiol-ene, and urethane acrylate systems. All of the systems evaluated exhibited shape memory behavior.

All of the thiol-vinyl systems exhibited excellent shape memory behavior. The urethane based thiol-vinyl systems (TMPTMP/TPDI6AE, IPDUT/IPDI6AE, and IPDI6AE/APE) exhibited excellent toughness (the ability to be handled and manipulated without breaking), as well. The urethane systems were tougher than the non urethane-containing systems. However, the mechanical property evaluations did not correlate well with observed polymer toughness.

Thiol-vinyl systems showed strong shape memory behavior once the polymers were heated above their glass transition temperatures. The glass transition temperature and widths were similar for both the urethane thiol-vinyl systems (TMPTMP/IPDI5AE, IPDUT/IPDI6AE, and IPDI6AE/APE) and the urethane acrylate system Ebecryl 8402. This data may indicate that both of these systems would exhibit similar shape memory response with temperature. However, the thiol-vinyl systems exhibited superior shape memory performance in regards to a lack of shape memory response below the glass transition temperature (visual observation) and a rapid transition above the glass transition temperature.

The tensile tests showed that, although the thiol-vinyl systems exhibited a uniformly strong shape memory response, there was a wide variation in the modulus, peak load capacity, and elongation of the polymers. This result was inconsistent with the qualitative observations of polymer toughness and shape memory behavior.

Thiol-vinyl polymer systems exhibit highly desirable polymer properties and shape memory behavior when compared with the acrylic-based polymers. Given the range of thiol and vinyl monomers, oligomers, and polymers that can be used in combination, it is possible to tailor systems to desired specifications for shape memory properties.

REFERENCES

[1]. T. Duerig, A. Pelton et al., "An overview of nitinol medical applications," Mater Sci Eng, A273-275 (1999), p. 149.

[2]. Liu C, Qin H et al, 2007 "Review of progress in shape-memory polymers" *Journal of Materials Chemistry*, DOI: 10.10391b615

[3]. Otsuka, K. and Wayman, C. M. (eds), 1998. Shape Memory Materials Cambridge University Press, Cambridge, UK

[4]. Lendlein A, Langer R, 2002, "Biodegradable, Elastic Shape-memory Polymers for Potential Biomedical Applications," *Science*, 296(5537):1673-1676

[5]. Lendlein A, Schimdt A M et al 2000 "AB-polymer networks based on oligo(E-caproloactone) segments showing shape memory property" *Proceedings of the National Academy of Sciences of the United States of America*, vol. 98, #3, 842-847

[6]. Lendlein A, Langer R, 2002, "Biodegradable, Elastic Shape-memory Polymers for Potential Biomedical Applications," *Science*, 296(5537):1673-1676

[7]. Flory 1953. P. J. Flory.: Principles of Polymer Chemistry, Cornell University Press, Ithaca, N.Y. (1953)

[8]. Ghosh, Samaresh "Recent research and development in synthetic polymer-based drug delivery systems" *Journal of Chemical Research*. April 2004 241-246(6)

[9]. K. Gall, C. M. Yakacki, Y. Liu, R. Shandas, N. Willett and K. S. Anseth "Thermomechanics of the shape memory effect in polymers for biomedical applications," *J. Biomed. Mater. Res.—Part A*, vol. 73, pp. 339, 2005.

[10]. Lu, H.; Carioscia, J. A.; Stansbury, J. W.; Bowman, C. N. Investigations of Step-Growth Thiol-Ene Polymerizations for Novel Dental Restoratives. *Dental Materials* 2005, 21, 1129-1136.

[11]. Yakacki C M, Shandas R, et al 2007, "Unconstrained recovery characterization of shape-memory polymer networks for cardiovascular applications", *J. Biomaterials*, vol 28, 255-2263.

[12]. Y. Liu, K. Gall, M. L. Dunn, P. McCluskey and R. Shandas "Shape memory polymers for medical applications," *Adv. Mater. Process.*, vol. 161, pp. 31, 2003.

[13]. Cramer N B, Bowman C B, 2001, "Kinetics of Thiol-Ene and Thiol-Acrylate Photopolymerizations with Real-Time Fourier Transform Infrared", *J. Polymer Science, Part A: Polymer Chemistry*, vol. 39, 3311-3319

[14]. C. R. Morgan, F. Magnotta and A. D. Ketley, Thiol-Ene photo-curable polymers, *J Polym Sci-Polym Chem* 15 (1977), pp. 627-645Hoyle C E, Lee T Y, Roper T, 2004, "Thiol-Enes: Chemistry of the Past with Promise for the Future", *J. Polymer Science: Part A: Polymer Chemistry*, vol. 43, 5501-5338 (2004)

[15]. Lu, H.; Carioscia, J. A.; Stansbury, J. W.; Bowman, C. N. Investigations of Step-Growth Thiol-Ene Polymerizations for Novel Dental Restoratives. *Dental Materials* 2005, 21, 1129-1136

[16]. Carioscia, J. A.; Schneidewind, L.; O'Brien, C.; Ely, R.; Feeser, C.; Cramer, N.; Bowman, C. N. "Thiol-Norbornene Materials: Approaches to Develop High $T_g$ Thiol-Ene Polymers" *Journal of Polymer Science Part-A Polymer Chemistry* 2007, 45, 5686-5696.

[17]. Baer G, Wilson T S, Matthews D L, Maitland D J: Shape-memory behavior of thermally stimulated polyurethane for medical applications. *J Appl Polym Sci* 2007, 103:3882-3892

[18]. Senyurt, A. F.; Hoyle, C. E.; Wei, H. Y.; Piland, S. G.; Gould, T. E. "Thermal and Mechanical Properties of Cross-linked Photopolymers Based on Multifunctional Thiol-Urethane Ene Monomers" *Macromolecules* 2007, 40(9), 3174-3182

[19]. Takahashi, T., Hayashi, N. and Hayashi, S. 1996. "Structure and Properties of Shape Memory Polyurethane Block Copolymers," Journal of Applied Polymer Science, 60(7): 1061-1069

[20]. Tao Fu, Jun-Liang Zhao, Ke-Wei Xu, The designable elastic modulus of 3-D fabric reinforced biocomposites, Materials Letters, Volume 61, Issue 2, January 2007, Pages 330-333, ISSN 0167-577X, DOI: 10.1016/j.matlet.2006.04.057.

[21]. Steven A. Koopmans, Thom Terwee, Jan Barkhof, Henk J. Haitjema, and Aart C. Kooijman:Polymer Refilling of Presbyopic Human Lenses In Vitro Restores the Ability to Undergo Accommodative Changes Invest. *Ophthalmol. Vis. Sci.*, January 2003; 44: 250-257.

We claim:

1. A medical device for in vivo medical applications comprising a shape memory polymer formed by polymerization of a mixture comprising:
a first monomer which does not homopolymerize and which has the structure of

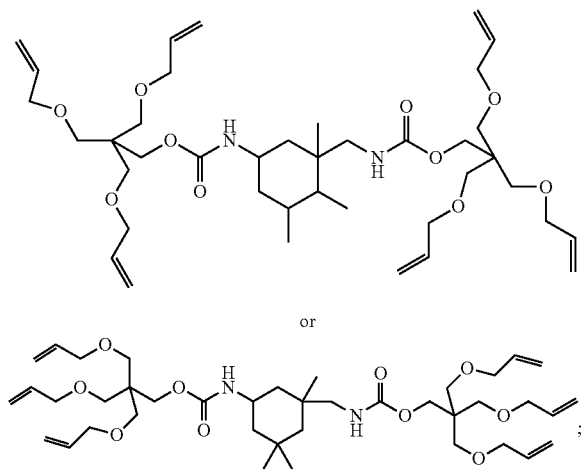

a second monomer or oligomer comprising at least three thiol groups; and
an optional third monomer or oligomer comprising at least one aliphatic carbon-carbon double bond
wherein the glass transition temperature of the polymer is from 25° C. to 45° C. and the strain to failure of the shape memory polymer is at least 40% as measured at 20-25° C.

2. The device of claim 1, wherein the third monomer or oligomer is homopolymerizable.

3. The device of claim 2, wherein the third monomer or oligomer comprises a plurality of urethane groups and a plurality of acrylate groups.

4. The device of claim 1, wherein the second monomer comprises from 2 to 6 thiourethane groups.

5. The device of claim 1 wherein the second monomer or oligomer is formed by reacting a polyisocyanate with a plurality of molecules comprising at least three thiol groups.

6. The device of claim 5 wherein the second monomer is a mixture of the reaction products of 2 equivalents of pentaerythritol tetra(3-mercaptopropionate) to 1 equivalent of isophorone diisocyanate.

7. The device of claim 1, wherein the device is an endoluminal prosthesis.

8. The device of claim 1, wherein the molar ratio of thiol groups in the mixture is from 30-70% and the molar ratio of aliphatic carbon-carbon double bonds and aliphatic carbon-carbon triple bonds groups in the mixture is from 70% to 30%.

9. The device of claim 2, wherein the thiol groups and non-homopolymerizable aliphatic carbon-carbon double bonds and aliphatic carbon-carbon triple bonds constitute greater than 30 mol % of the mixture.

10. The device of claim 1, wherein the molecular weight of the first monomer is from 200 to 2000.

11. The device of claim 1, wherein the molecular weight of the second monomer is from 200 to 2000.

12. The device of claim 1 wherein the shape memory polymer is biodegradable.

13. The device of claim 12, wherein the shape memory polymer degrades by hydrolysis by exposure to water or enzymes under physiological conditions.

14. A medical device for in vivo medical applications comprising a shape memory polymer formed by polymerization of a mixture comprising:
   a first monomer or oligomer comprising at least three aliphatic carbon-carbon double bonds or at least three aliphatic carbon-carbon triple bonds;
   a second monomer or oligomer comprising at least six thiol functional groups; and
   an optional third monomer or oligomer comprising at least one aliphatic carbon-carbon double bond
   wherein at least one of the monomers or oligomers in the mixture further comprises at least one urethane or thiourethane group, the glass transition temperature of the polymer is from 25° C. to 45° C. and the strain to failure of the shape memory polymer is at least 40% as measured at 20-25° C.

15. The medical device of claim 1 wherein the first monomer has the following structure:

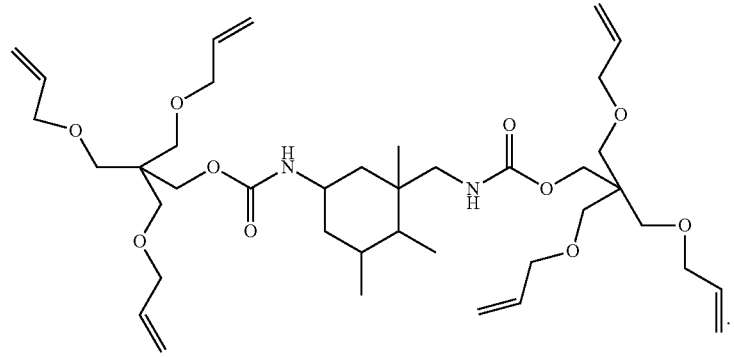 [SMILES: C=CCOCC(COCC=C)(COCC=C)COC(=O)NCC1(C)CC(NC(=O)OCC(COCC=C)(COCC=C)COCC=C)CC(C)C1C]

16. The medical device of claim 1 wherein the first monomer has the following structure:

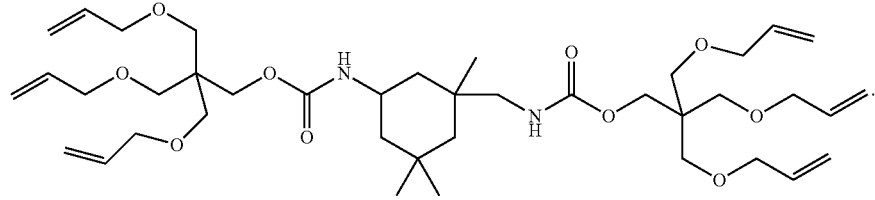 [SMILES: C=CCOCC(COCC=C)(COCC=C)COC(=O)NCC1(C)CC(NC(=O)OCC(COCC=C)(COCC=C)COCC=C)CC(C)(C)C1]

* * * * *